(12) United States Patent
Scott et al.

(10) Patent No.: US 11,826,159 B2
(45) Date of Patent: Nov. 28, 2023

(54) BRAIN MONITORING SYSTEM

(71) Applicant: JUNEBRAIN INC., Rockville, MD (US)

(72) Inventors: Samantha I. Scott, Rockville, MD (US); Al-Hafeez Dhalla, Durham, NC (US); Audrey Bowden, Nashville, TN (US)

(73) Assignee: JUNEBRAIN INC., Rockville, MD (US)

( * ) Notice: Subject to any disclaimer, the term of this patent is extended or adjusted under 35 U.S.C. 154(b) by 141 days.

(21) Appl. No.: 17/106,962

(22) Filed: Nov. 30, 2020

(65) Prior Publication Data

US 2021/0186408 A1 Jun. 24, 2021

Related U.S. Application Data

(62) Division of application No. 15/971,740, filed on May 4, 2018, now Pat. No. 10,849,547.

(60) Provisional application No. 62/501,482, filed on May 4, 2017.

(51) Int. Cl.
*A61B 5/00* (2006.01)
*A61B 3/10* (2006.01)
(Continued)

(52) U.S. Cl.
CPC .......... *A61B 5/4064* (2013.01); *A61B 3/0025* (2013.01); *A61B 3/102* (2013.01); *A61B 3/12* (2013.01); *A61B 3/1225* (2013.01); *A61B 3/14* (2013.01); *A61B 5/0071* (2013.01); *A61B 5/4076* (2013.01); *A61B 34/25* (2016.02); *A61B 5/0013* (2013.01); *A61B 5/0022* (2013.01); *A61B 5/0066* (2013.01); *A61B 2034/256* (2016.02); *A61B 2090/3735* (2016.02); *A61B 2090/502* (2016.02); *A61B 2576/026* (2013.01)

(58) Field of Classification Search
CPC ... A61B 5/4064; A61B 5/0071; A61B 5/4076; A61B 5/0013; A61B 5/0022; A61B 5/0066; A61B 3/0025; A61B 3/102; A61B 3/12; A61B 3/14; A61B 3/1225; A61B 34/25; A61B 2034/256; A61B 2090/3735; A61B 2090/502; A61B 2576/026
USPC ......................................................... 351/206
See application file for complete search history.

(56) References Cited

U.S. PATENT DOCUMENTS 6,003,991 A 12/1999 Viirre
6,485,413 B1 11/2002 Boppart et al.
(Continued)

FOREIGN PATENT DOCUMENTS

EP 2142076 B1 4/2016
GB 2317227 A 3/1998
(Continued)

OTHER PUBLICATIONS

International Search Report and Written Opinion for PCT Patent App. No. PCT/US18/31171 (dated Sep. 13, 2018).
(Continued)

*Primary Examiner* — Collin X Beatty
(74) *Attorney, Agent, or Firm* — JONES ROBB, PLLC

(57) ABSTRACT

Systems and methods capture light reflected back from a patient's fundus and compares the resulting images to prior images, to determine if the patient is experiencing intraocular inflammation or atrophy.

18 Claims, 16 Drawing Sheets

(51) Int. Cl.
*A61B 3/12* (2006.01)
*A61B 3/14* (2006.01)
*A61B 3/00* (2006.01)
*A61B 34/00* (2016.01)
*A61B 90/50* (2016.01)
*A61B 90/00* (2016.01)

(56) References Cited

U.S. PATENT DOCUMENTS

| | | | |
|---|---|---|---|
| 8,526,472 B2* | 9/2013 | Flanders | G01B 9/02004 372/24 |
| 9,457,253 B1 | 10/2016 | Rodriguez | |
| 9,696,132 B2* | 7/2017 | Jayaraman | A61B 3/102 |
| 9,888,841 B2 | 2/2018 | Hogan | |
| 2002/0036750 A1 | 3/2002 | Eberl et al. | |
| 2004/0036838 A1* | 2/2004 | Podoleanu | A61B 3/1025 351/206 |
| 2006/0215113 A1 | 9/2006 | Chernyak | |
| 2007/0046948 A1 | 3/2007 | Podoleanu et al. | |
| 2009/0213282 A1 | 8/2009 | Burlingame et al. | |
| 2009/0244485 A1 | 10/2009 | Walsh et al. | |
| 2010/0278394 A1 | 11/2010 | Raguin et al. | |
| 2013/0120711 A1* | 5/2013 | Hacker | A61B 5/0066 351/206 |
| 2013/0229620 A1 | 9/2013 | Hammer et al. | |
| 2013/0295014 A1 | 11/2013 | Boyd | |
| 2015/0223683 A1 | 8/2015 | Davidovics et al. | |
| 2015/0272435 A1 | 10/2015 | Ito et al. | |
| 2016/0143539 A1* | 5/2016 | Koerner | A61B 5/0086 600/475 |
| 2016/0270656 A1* | 9/2016 | Samec | A61M 21/02 |
| 2017/0049318 A1 | 2/2017 | Walsh et al. | |
| 2017/0311796 A1 | 11/2017 | Walsh et al. | |
| 2017/0345391 A1 | 11/2017 | Usui et al. | |
| 2018/0107025 A1 | 4/2018 | Smit et al. | |
| 2018/0184897 A1 | 7/2018 | Yamamoto et al. | |
| 2018/0270474 A1* | 9/2018 | Liu | A61B 6/508 |
| 2018/0333092 A1 | 11/2018 | Roshan et al. | |

FOREIGN PATENT DOCUMENTS

| | | |
|---|---|---|
| WO | WO98/07022 A1 | 2/1998 |
| WO | WO2015/185622 A2 | 12/2015 |

OTHER PUBLICATIONS

Guay-Lord, R., et al., "Combined optical coherence tomography and hyperspectral imaging using a double-clad fiber coupler," J. Biomed. Optics 2016;21(11):116008-1-116008-6.

Kim, S., et al., "Design and implementation of a low-cost, portable OCT system," Biomed. Optics Express 2018;9(3):1232-1243.

Lu, C. D., et al., "Handheld ultrahigh speed swept source optical coherence tomography instrument using a MEMS scanning mirror," Biomed. Optics Express 2014;5(1):293-311.

Maloca, P., et al., "Safety and Feasibility of a Novel Sparse Optical Coherence Tomography Device for Patient-Delivered Retina Home Monitoring," TVST 2018;7(4), Article 8, pp. 1-12.

McNamera, P. M., et al., "Development of a first-generation miniature multiple reference optical coherence tomography imaging device," J. Biomed. Optics 2016;21(12):126020-1-126020-7.

Ryu, S. Y., et al., "Combined system of optical coherence tomography and fluorescence spectroscopy based on double-cladding fiber," Optics Lett. 2008;33(20):2347-2349.

3D OCT-2000 FA plus. Topcon. Cited Dec. 2, 2017. Available from: http://www.topcon.co.jp/en/eyecare/products/product/diagnostic/oct/3DOCT-2000_E.html, retrieved from the internet Oct. 23, 2018, 2 pp.

D-EYE Portable Retinal Imaging System. D-EYE Srl. Cited Aug. 31, 2017. Available from: https://www.d-eyecare.com/en_US#vision, retrieved from the internet Oct. 23, 2018, 6 pp.

Pictor Plus Ophthalmic Camera. Volk Optical, Inc. Cited Dec. 2, 2017. Available from: https://volk.com/index.php/volk-products/ophthalmic-cameras/volk-pictor-plus-digital-ophthalmic-imager.html, retrieved from the internet Oct. 23, 2018, 15, pp.

Visuscout 100 Handheld Fundus Camera. Carl Zeiss Meditec, Inc. Cited Dec. 2, 2017. Available from: https://www.zeiss.com/meditec/us/products/ophthalmology-optometry/essential-line-basic-diagnostics/iop-and-retina-screening/visuscout-100.html, retrieved from the internet Oct. 23, 2018, 2 pp.

The Horus Scope. Jedmed. Cited Dec. 2, 2017. Available from: https://www.jedmed.com/products/portable-fundus-camera, retrieved from the internet Oct. 23, 2018, 2 pp.

Envisu C2300. Leica Microsystems. Cited Aug. 31, 2017. Available from: https://www.leica-microsystems.com/fileadmin/downloads/Envisu%20C2300/Brochures/Envisu_C2300_PrintBrochure_en.pdf, retrieved from the internet Oct. 23, 2018, 8 pp.

IScan. Optovue, Inc. Cited Dec. 2, 2017. Available from: http://www.optovue.com/products/iscan/, retrieved from the internet Oct. 23, 2018, 3 pp.

Heidelberg Engineering. Spectralis. Cited Apr. 3, 2018. Available from: https://business-lounge.heidelbergengineering.com/us/en/products/spectralis/spectralis/, retrieved from the internet Oct. 23, 2018, 4 pp.

International Preliminary Report Aon Patentability for PCT Patent App. No. PCT/US18/31171 (dated Aug. 23, 2019).

European Search Report dated May 17, 2021 for EP Application No. 18793948.3, 12 pages.

* cited by examiner

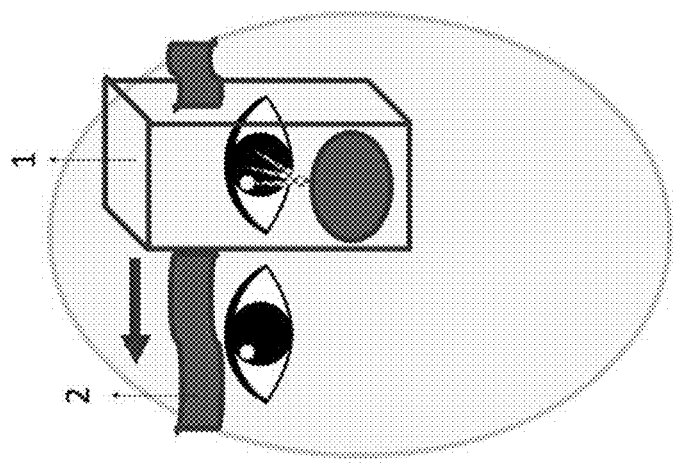
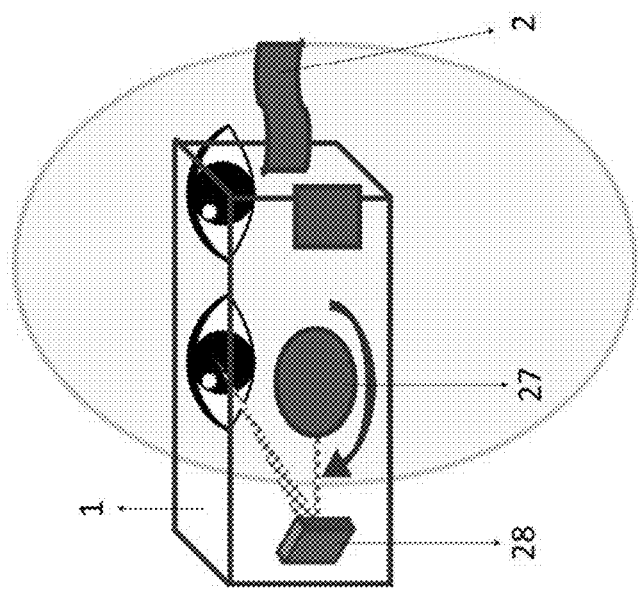
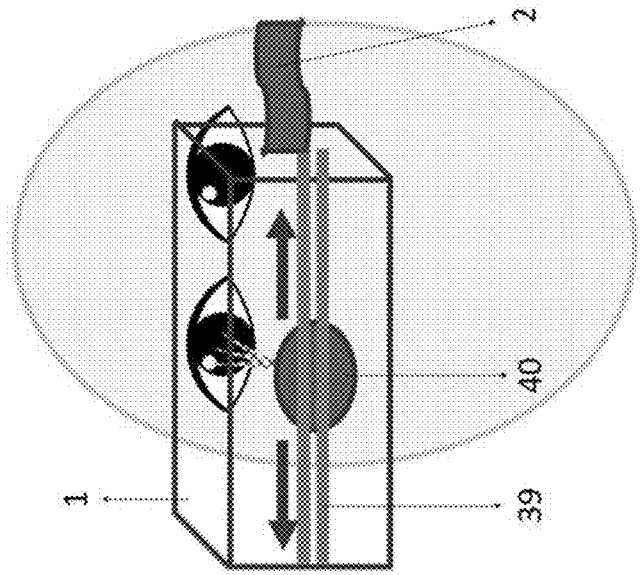
FIG. 15C
FIG. 15B
FIG. 15A

BRAIN MONITORING SYSTEM

This application is a divisional application of U.S. application Ser. No. 15/971,740, filed May 4, 2018, now U.S. Pat. No. 10,849,547, which claims priority to U.S. Provisional Application No. 62/501,482 filed 4 May 2017, each of which is hereby incorporated by reference in its entirety.

BACKGROUND

Field of Endeavor

This application's subject matters relate to systems and methods for monitoring brain and retina function of a patient.

Brief Description of the Related Art

Inflammation is a hallmark of eye and brain damage and is implicated in such common retinal diseases as age-related macular degeneration (AMD) and glaucoma, as well as a range of brain ailments from multiple sclerosis (MS) to traumatic brain injury (TBI). Studies have further established a relationship between inflammation in the retina and brain disease progress, such that worsening of neuroinflammation often precedes the onset of patient symptoms. These include an association between increased retinal layer thickness (possibly representing inflammation) and MS disease activity [1], the detection of a cortical immune response in the retina following an epileptic seizure [2], and increased inflammation in the retinas of rats with repetitive mild traumatic brain injuries (mTBI) [3]. Evidence from MS studies also suggests that inflammatory processes in specific retinal layers may inform specific cortical disease processes [1]. However, gold standard approaches for monitoring these conditions are often invasive, expensive, and limited to specialized healthcare facilities.

Given the impact of inflammation on brain and ocular function and patient prognosis, a critical need exists for a device that enables patients with neuroinflammatory conditions to measure changes in their retinal pathology at home, thus allowing their physicians to objectively and more frequently monitor patients' disease activity remotely. Fundus autofluorescence (FAF) and optical coherence tomography (OCT) are both non-invasive retinal imaging modalities that can be used for this purpose.

Fundus autofluorescence (FAF) is a safe, non-invasive modality that uses fundus photography to identify regions of the retina with increased accumulation of lipofuscin—a natural fluorophore located in neurons of the retina and cortex. Lipofuscin accumulation (presenting as increased autofluorescence) is indicative of activated microglia activity [4], where structures containing lipofuscin (such as the retina's RPE layer) are phagocytized and released or accumulated in macrophages. This increased accumulation is thus a sign of degeneration, inflammation, infection, and/or toxicity.

Autofluorescence occurs when fluorophores absorb and then emit a specific wavelength of light. Traditional FAF uses a blue light (~470 nm) to excite lipofuscin in the retina, and collects the resulting emissions using a filter and detector that are preset to the relevant spectra (600-610 nm). A brightness map can then be created that illustrates the distribution and density of lipofuscin across the retina and thus pinpoint areas that are abnormal.

Optical coherence tomography (OCT) is similarly a widely-used, non-invasive modality for imaging the retina. While FAF focuses on functional mapping of the retina, OCT provides structural images of the retinal surface and layers. The technique is based on low-coherence interferometry, in which reflected light from a reference arm (i.e., mirror) and sample are combined to create an interference pattern. When the reference mirror is scanned (e.g., using a micro-electro-mechanical system [MEMS] scanner), interference patterns across the sample can be generated, resulting in a series of axial depth scans (A-scans). Multiple A-scans over a transverse line can then be combined to create cross-sectional (B-scan) structural images of the sample. While time-domain OCT (TD-OCT) uses a scanning reference mirror, swept-source Fourier-domain OCT (SS FD-OCT) uses a tunable laser that quickly sweeps through a narrow band of wavelengths to acquire A-scan images (the reference mirror remains fixed).

In the case of the retina, OCT images can indicate changes in the thickness of specific retinal layers due to atrophy or inflammation. Studies have further identified a correlation between OCT and FAF measures in retinal diseases, where changes in autofluorescence were associated with (and may serve as a predictor of) the progression of geographic atrophy or inflammation [5,6].

Currently available systems for combination OCT and FAF imaging by eye care professionals include Zeiss' CIRRUS Photo 80028 [7], Heidelberg Engineering's Spectralis Diagnostic Imaging Platform [8], and Topcon's 3D OCT-2000 FA plus [9]. A new portable OCT space is also gaining traction that includes several marketed products. Handheld OCT and fundus devices are designed for use by healthcare providers for screening and evaluation of retinal diseases in non-traditional settings, including the D-EYE Portable Retinal Imaging System [10], Volk Pictor Plus handheld fundus camera [11], Zeiss' Visuscout 100 handheld fundus camera [12], Jedmed's Horus Scope handheld fundus camera [13], and Envisu C2300 handheld OCT system from Leica Microsystems (a technology acquired from their acquisition of Bioptigen, Inc.) [14]. Though not handheld, Optovue's iVue and iFusion comprise a portable OCT and fundus camera combination system currently on the market [15].

Several other portable technologies have been developed by research groups but do not have FDA approval, including portable OCT systems for use during surgery and on infants and children in the clinical setting. A tabletop Spectralis OCT system was modified into a handheld unit by Vinekar et al. and used to image retinal pathology in infants [16], while two groups integrated OCT into a microscope for interoperative use [17,18]. Lu et al. further developed an ultrahigh speed, handheld OCT instrument using a MEMS scanning mirror [19]. Development of a low-cost, portable OCT system was recently demonstrated by Kim et al. [20].

SUMMARY

While the devices described above can be used to measure retinal pathology, the subject matter described in this application includes at least the following differences, which can be key in certain applications:

1. It is specifically designed for patient use at home, including ruggedization of the system components for durability under a range of temperatures, pressures, humidity, shock, and accelerations.

2. It can include a modular design—including a headset unit—that allows the imaging interface to be attached directly to the patient, significantly reducing motion artifacts and the need for re-imaging. The headset has a lightweight, ergonomic design and includes a blackout component that allows a user's eye to naturally dilate after donning the headset, for non-mydriatic OCT and FAF imaging.

3. In one exemplary design, it utilizes a motorized flip mirror that directs a beam of light to and from the user's right or left eye of the headset for sequential imaging of each eye.

4. In one exemplary design, double-cladding fiber can be used to implement an all-fiber OCT/FAF system to achieve simultaneous OCT and FAF image acquisition.

5. It can include automated image acquisition, processing, analysis, and transmission of results from the device to a clinician in a HIPPA-compliant manner for remote assessment of retinal pathology. Data can advantageously be stored on a cloud server.

6. It can include image processing software to automatically make specific adjustments that compensate for the distance between a user's eyes, pupil size, light levels, etc.

7. It can include voice commands to guide the user through the image acquisition process.

8. It can include a mobile software application that presents changes in results over time to the user and/or a clinician for regular monitoring of disease activity.

9. It can use a combined FAF and OCT image analysis routine to track active changes in inflammatory activity within specific retinal layers; FAF can detect functional changes in retinal inflammation that occur before a structural change can be identified with OCT, leading to earlier detection of retinal pathology changes.

According to a first aspect of the invention, a system useful for FAF and OCT image acquisition of a patient's eye comprises a broadband LED as an FAF light source, a tunable laser as an OCT light source, a coupler, a first lightpath communicating visible light from the broadband LED, the first lightpath including an excitation filter, the first lightpath communicating light from the excitation filter to the coupler, a second lightpath communicating near infrared light from said tunable laser to said coupler, wherein the coupler combines light from said first and second lightpaths, a single-mode fiber receiving light from said coupler, a splitter receiving light form said single-mode fiber, third and fourth lightpaths receiving light from said splitter, a reference arm in said third lightpath, and a headset sample arm in said fourth lightpath.

According to another aspect of the present invention, an image acquisition headset comprises at least one goggle configured to fit over a portion of a patient's face and cover at least one eye, a strap attached to the at least one goggle for securing said at least one goggle to the patient's head, an image data acquisition module comprising a lightpath having a broadband light source, a first aperture, a lens system including a first beam splitter, an autofocus lens, a secondary aperture, second beam splitter, a camera, and a signal processing unit in electrical communication with said camera.

According to yet another aspect of the present invention, a process of FAF and OCT image acquisition of a patient's eye comprises generating light with a broadband LED and tunable laser, wherein visible light from the broadband LED first travels through a lipofuscin excitation filter, combining light from said excitation filter with near infrared light from said tunable laser, splitting and transmitting light from said combining step to a reference arm, and a headset sample arm configured to be positioned in front of a patient's eye.

Still other aspects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to exemplary embodiments of the apparatus and method, given only by way of example, and with reference to the accompanying drawings, in which:

FIGS. 15A, 15B, and 15C Illustrate three additional configurations of the headset, in which only a single imaging element is used.

DETAILED DESCRIPTION OF EXEMPLARY EMBODIMENTS

Figure 1A:
FIG. 1A illustrates the headset-only version of a system embodying principles of the present disclosure.

Referring to the drawing figures, like reference numerals designate identical or corresponding elements throughout the several figures.

The singular forms "a," "an," and "the" include plural referents unless the context clearly dictates otherwise. Thus, for example, reference to "a solvent" includes reference to one or more of such solvents, and reference to "the dispersant" includes reference to one or more of such dispersants.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

For example, a range of 1 to 5 should be interpreted to include not only the explicitly recited limits of 1 and 5, but also to include individual values such as 2, 2.7, 3.6, 4.2, and sub-ranges such as 1-2.5, 1.8-3.2, 2.6-4.9, etc. This interpretation should apply regardless of the breadth of the range or the characteristic being described, and also applies to open-ended ranges reciting only one end point, such as "greater than 25," or "less than 10."

Generally, the devices and systems described herein, are wearable, non-invasive, and non-mydriatic systems that image the user's retina and use FAF, OCT, or FAF and OCT to measure and/or identify layer-specific retinal pathology (e.g., retinal inflammation and degeneration) to help track the progression of eye and brain health. While OCT and FAF have been modalities for imaging the retina, they have not yet been made available for disease monitoring at home. The systems and methods described herein are significantly different from commercially available retinal imaging systems in that they are 1) designed specifically to permit an individual to use at home, 2) include automated image acquisition for ease of use by the user, and 3) transmit image data results to a clinician in a secure (e.g., U.S.'s HIPPA laws and regulations) and compliant manner for regular, remote assessment of disease activity in their patients.

Several exemplary embodiments of the invention are depicted in the figures and described below.

Overall Device Use

FIG. 1 illustrates a headset-only version of a system embodying principles of the present invention, including: A) headset device, B) patient mobile software user interface showing a graphical illustration of changes in FAF/OCT measures over time (including bottom buttons for a user dashboard [left], window to input changes in symptoms [left center] and medications [right center], and a community discussion board [right]) (10), and C) illustration of a user wearing the system and holding a mobile device that includes the software shown in B.

Figure 14:
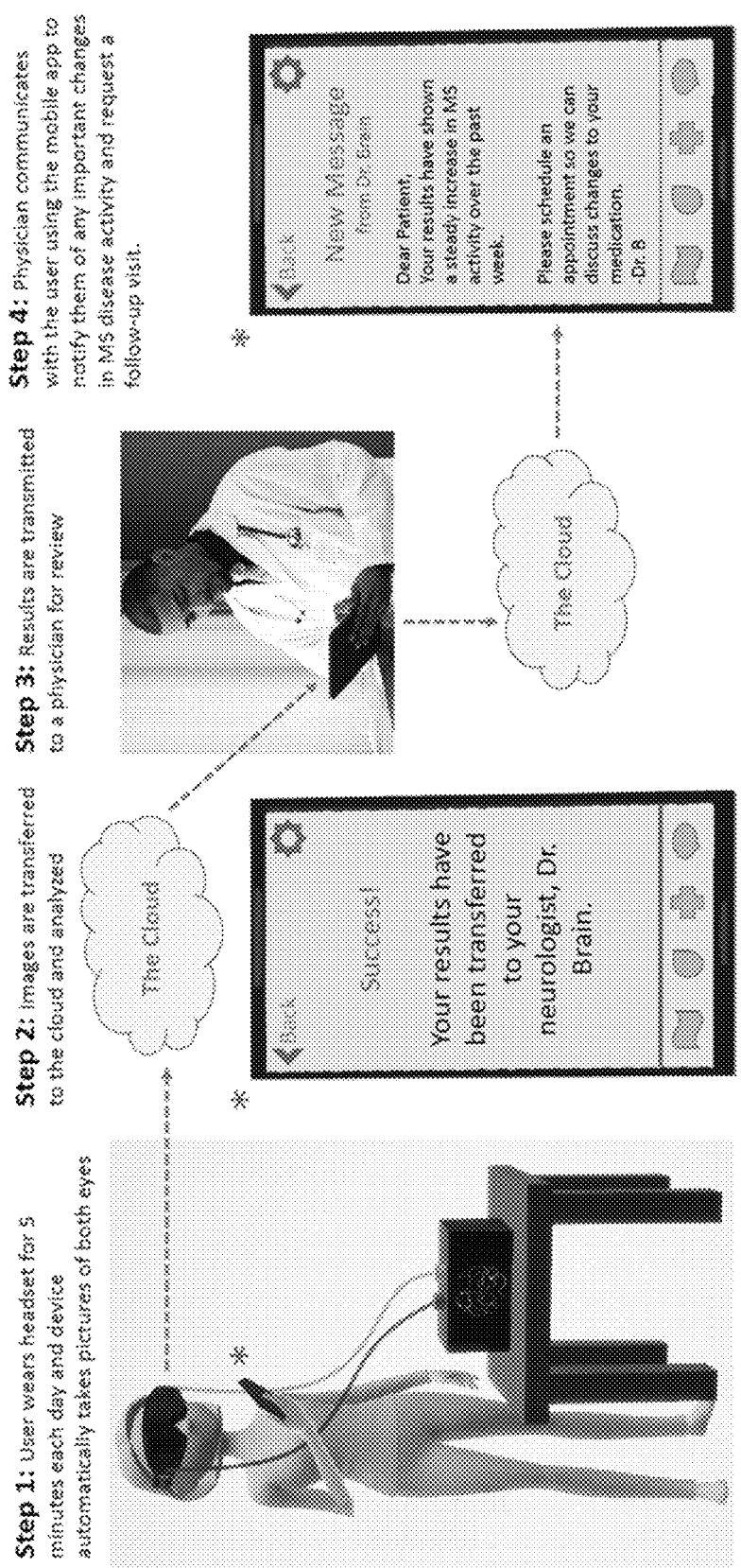
FIG. 14 Illustrates an example workflow for the invention, including data acquisition by the patient, analysis, and transfer to a clinician.

In this exemplary embodiment, the headset (1) is lightweight, ergonomic, and designed to be worn over the user's eyes with scanning hardware to image each eye (see FIGS. 1 and 14). It includes adjustable straps (2), a USB port for battery charging (3), a blackout component that allows users' eyes to naturally dilate after donning the headset (that is, the 'lens' of the goggle is entirely opaque, and the goggle conforms to the wearer's face and forehead so that little or no ambient light enters the goggles when worn) (4), On/Off power button (5), "Acquire Image" button for signaling to the control system to initiate manual image acquisition (6), button to signal to the control system to toggle between "Manual" and "Automatic" image acquisition modes (7), a fixation target (e.g., red light) for user fixation during image acquisition (8), and lens opening for each eye that allows images to be acquired of each (9). The headset is durable (e.g., according to the U.S.'s MIL-STD-810 standards for ruggedization under various temperature, shock, humidity, pressure, and acceleration conditions) and may include different color and texture straps for aesthetics and user personalization. Buttons (5-7), to activate the system, will be easily distinguished by touch.

Image Acquisition Process

Figure 2:
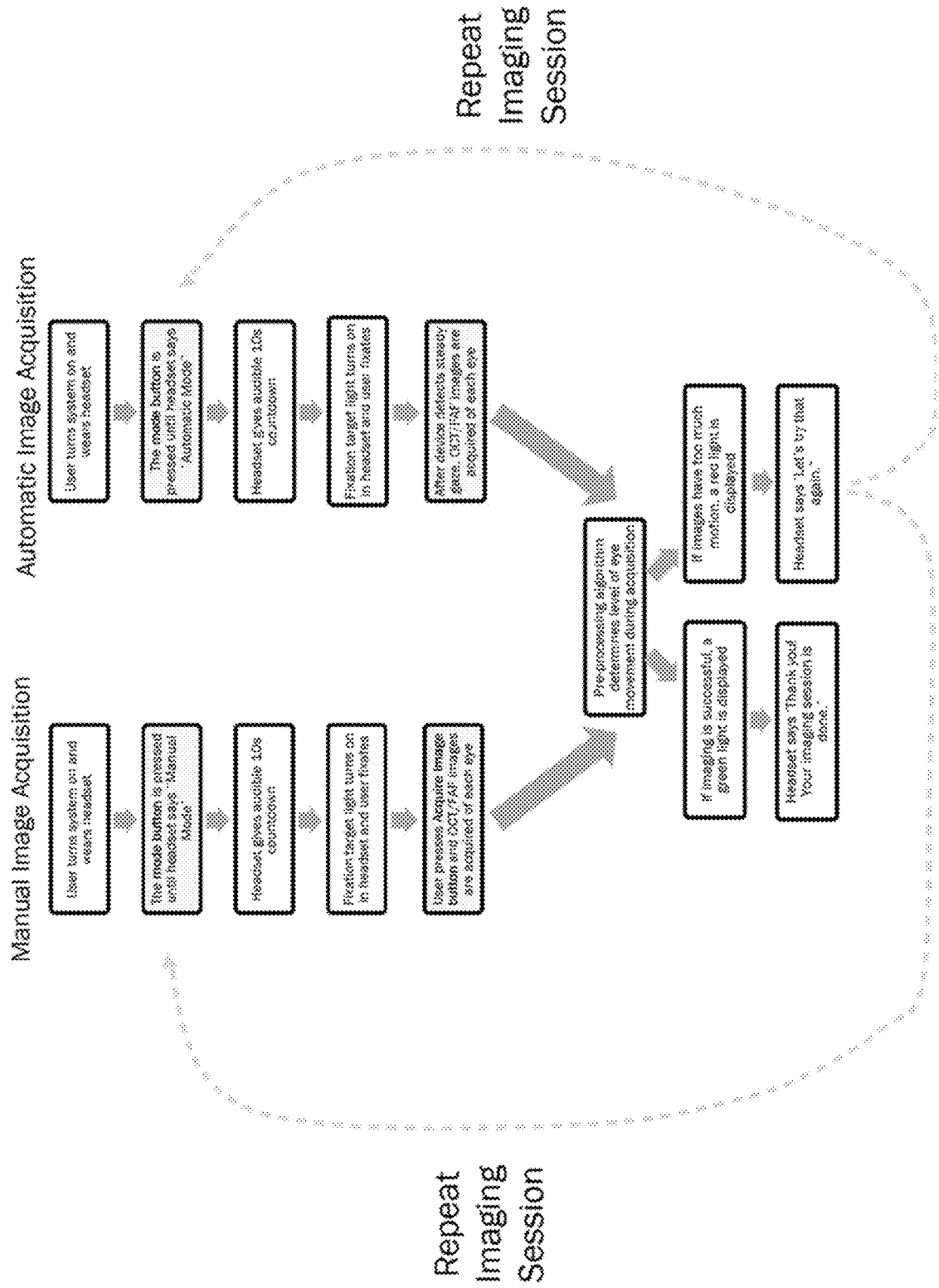
FIG. 2 illustrates manual vs. automatic image acquisition processes.

FIG. 2 illustrates the steps a user will follow to use the device in either manual (A) or automatic (B) image acquisition modes. Users will use the system by wearing the device's headset briefly on a regular basis (e.g., daily, weekly, or bi-weekly). After turning the system on and donning the headset, if manual mode is chosen using the mode button, the user will hear an audible 10 second (for example) countdown from "ten" to "one" (which provides time for the user's eye to naturally dilate in darkness; this voice instruction may come from the device, mobile software application, or the like), after which a fixation target (e.g., red light) will turn on in the headset. The user-after they are ready and steadily fixated on the red light—will then press the "Acquire Image" button to signal to the control system to initiate the image acquisition process, during which time fundus, OCT, and/or FAF images will be acquired sequentially or simultaneously from each eye. The system automatically makes specific adjustments to compensate for the distance between the user's eyes, pupil size, light levels, etc.

After turning the system on and donning the headset, if automatic mode is chosen using the mode button, the user will hear an audible 10 second (for example) countdown from "ten" to "one". A fixation target will then turn on in the headset and an eye tracking algorithm will be used to detect the user's pupil and determine when the user's gaze is fixated (where, for example, fixation is defined as a gaze remaining within a diameter of 1° visual angle for at least 100 ms). After fixation is detected, the device will automatically initiate the image acquisition process.

In both manual and automatic modes, voice commands will guide the patient through the image acquisition process. This will include the device informing the user if an image set was successfully acquired, or if re-imaging is required (as determined by the level of eye movement detected during pre-processing, see FIGS. 5A-B), as well as when the user has completed their imaging session and can remove the headset.

Figure 3A:
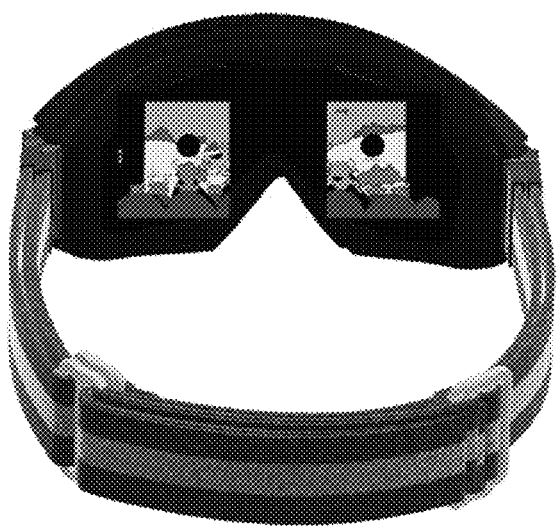
FIG. 3A illustrates a headset of the system of FIG. 1A configured for use of a virtual reality function.
Figure 3B:
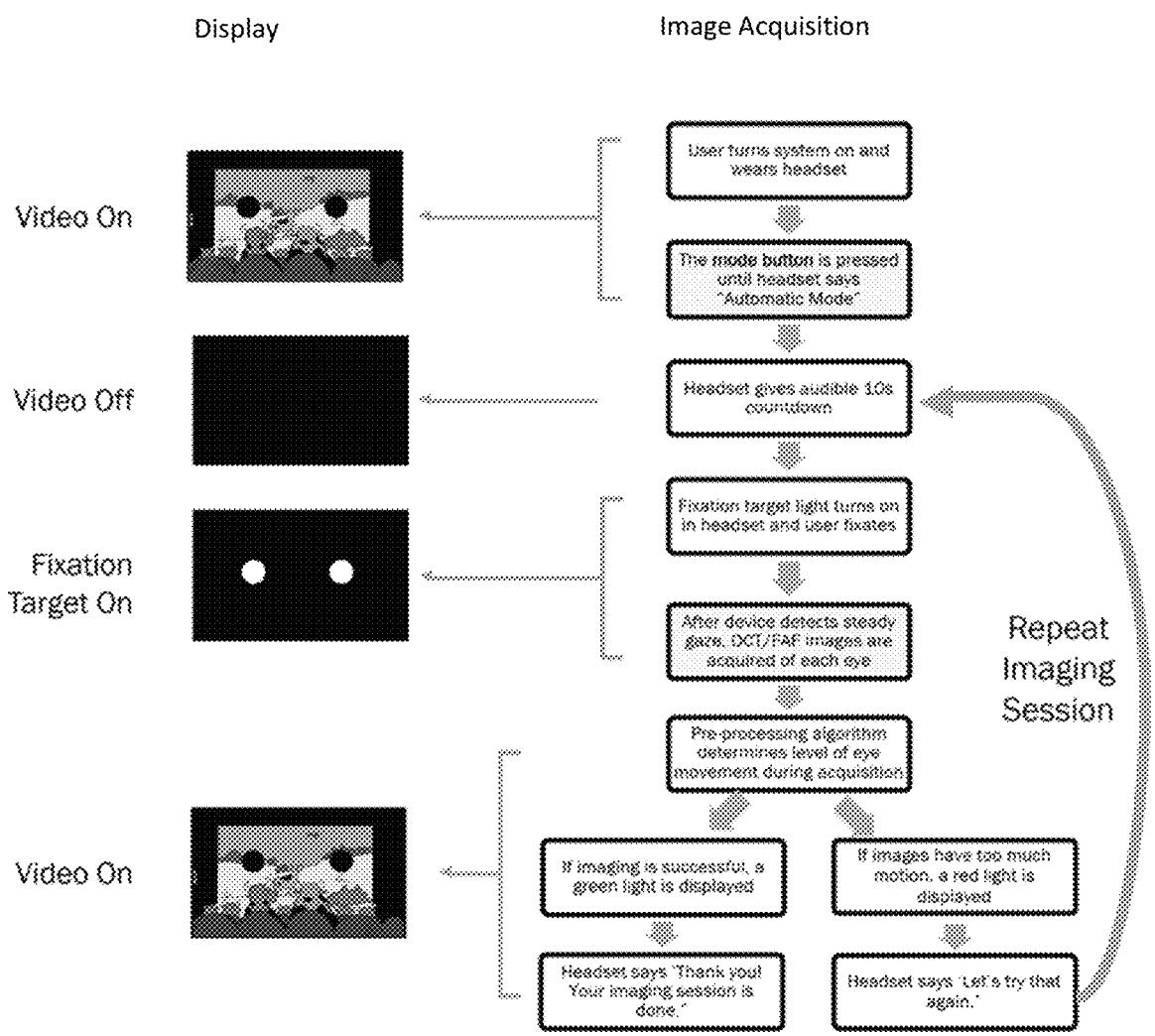
FIG. 3B illustrates a workflow for use of a virtual reality function to engage the user during image acquisition.

FIG. 3 illustrates a further exemplary embodiment of the invention, in which the headset also includes a video function that provides the user with a form of virtual reality entertainment during the image acquisition process to help the user remain engaged until images have been successfully acquired. In this version of the headset (see FIG. 3A), one or two displays (one for each eye, e.g., LCD, OLED, and the like) are located inside the headset goggles. Lenses are placed between the displays and the user's eyes, where the distance between the lenses and eyes can be manually adjusted by the user until the displays' images are clear. The displays each include a central opening, through which the scanning hardware can image each eye, or for displays formed of transparent or semi-transparent material, the scanning hardware does not require a central opening and scans directly through the display itself. After the user has donned the headset and switched the device to automatic mode, a video will be played for a brief period of time, after which the screen will turn off and an audible countdown will commence. As an example (see FIG. 3B), the video may show one or more of the following:

1. A cartoon character walking into a movie theater with a bucket of popcorn
2. After finding their seat in the theater, the character sits down and the lights in the theater begin to dim in preparation for the movie 3. Once the theater lights are off, the display(s) will also turn off in the headset and an audible countdown will commence for the user 4. A red fixation light will be displayed through the central opening of the display(s) (or through the transparent or semi-transparent material) and, once the user is fixating, images will automatically be acquired from each eye 5. After image acquisition, the displays will turn on again and show the character watching a movie playing on the theater screen. During this time, pre-processing algorithms will determine if the images are acceptable (e.g., if a non-significant amount of motion is detected) and either inform the user (using auditory and/or visual cues) that the imaging session is complete or a re-scan is required.

6. In the case of a re-scan, the light in the theater on the display video will once again dim, and steps 3-5 will be repeated.

Other video content, other than a movie theater, can be displayed instead of, or in addition to, the exemplary movie theater example.

Data Storage and Transmission

Figure 4:
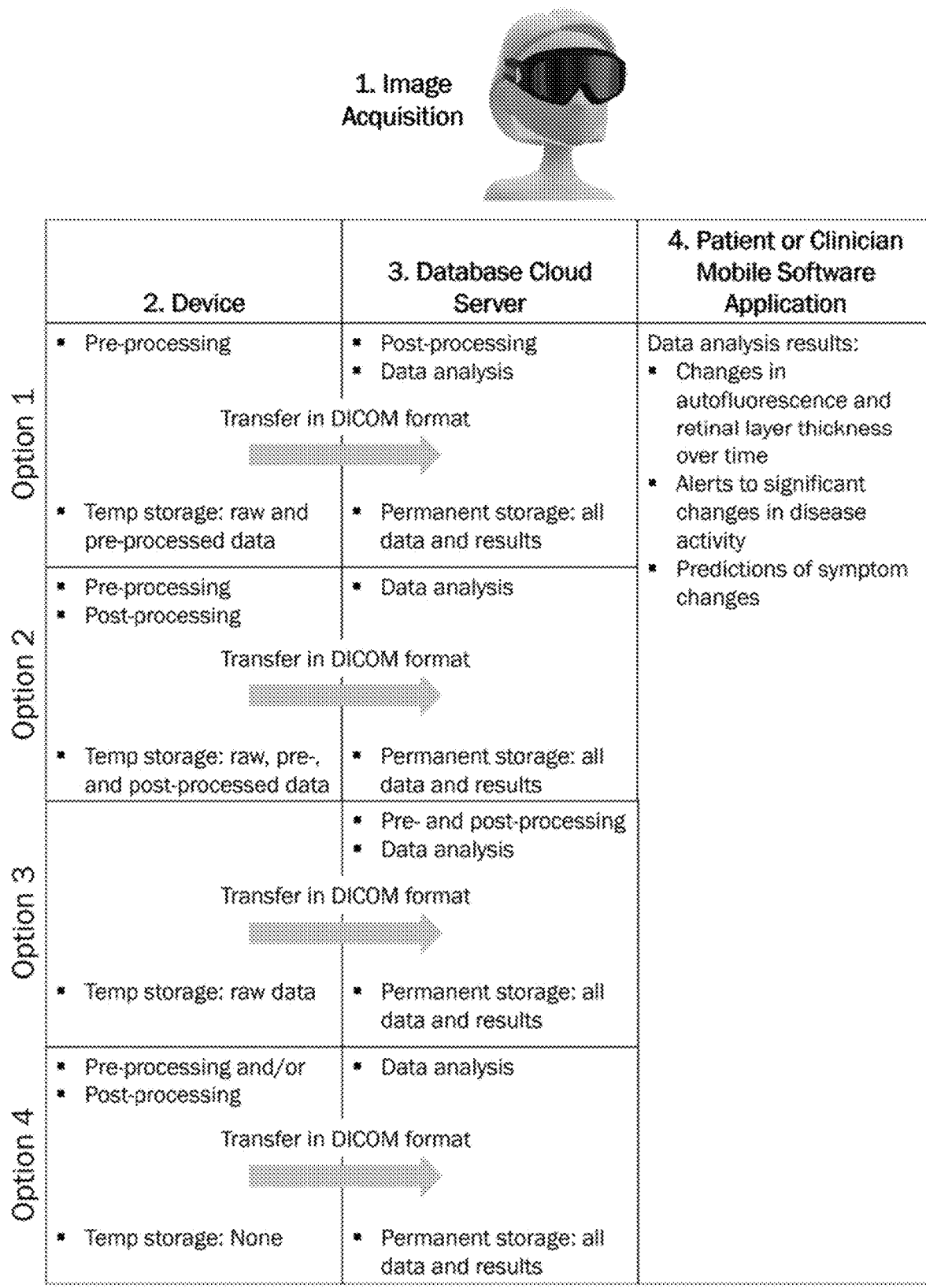
FIG. 4 Illustrates data storage and transmission among devices.

FIG. 4 illustrates how data may be stored and transmitted following a user's imaging session. After image acquisition (see FIG. 5), image data (e.g., in DICOM format) may follow one of several pathways, where data processing and analysis will be automated by a series of image processing algorithms:

Option 1. The data may be immediately pre-processed on the device (see FIG. 5), transferred to a database server in the cloud for further post-processing and analysis (see FIGS. 5 and 6), and results outputted (e.g., wirelessly) to the user and/or a clinician's mobile software application. In this case, a limited amount of raw and pre-processed data (e.g., 1 month's worth of imaging sessions) can be temporarily stored on the device and—after a period of time or after reaching a device storage limit—transferred (e.g., wirelessly) to the database cloud server for permanent storage with the post-processed data and analyzed results.

Option 2. The data may undergo pre- and post-processing on the device, after which it is transferred to a database server in the cloud for analysis, and results outputted (e.g., wirelessly) to the user and/or a clinician's mobile software application. In this case, a limited amount of raw, pre-, and post-processed data can be temporarily stored on the device and—after a period of time or after reaching a device storage limit—transferred (e.g., wirelessly) to the database cloud server for permanent storage with the analyzed results.

Option 3. In yet further embodiments, pre-processing can be performed at the (cloud) server level, with the raw data being communicated to that server without preprocessing. In this case, the device will communicate with the server to obtain the amount of eye movement detected in the images (as calculated during pre-processing)—this information will be used by the device to determine whether the imaging session was successful or if a re-scan is needed.

Option 4. Furthermore, raw and/or pre- and/or post-processed data can optionally not be stored for significant time periods on the data capturing system itself, instead being stored at the server level, the data capture system storing the data locally only for time sufficient to transmit that data upstream towards the server level.

Data Processing and Analysis

Figure 5:
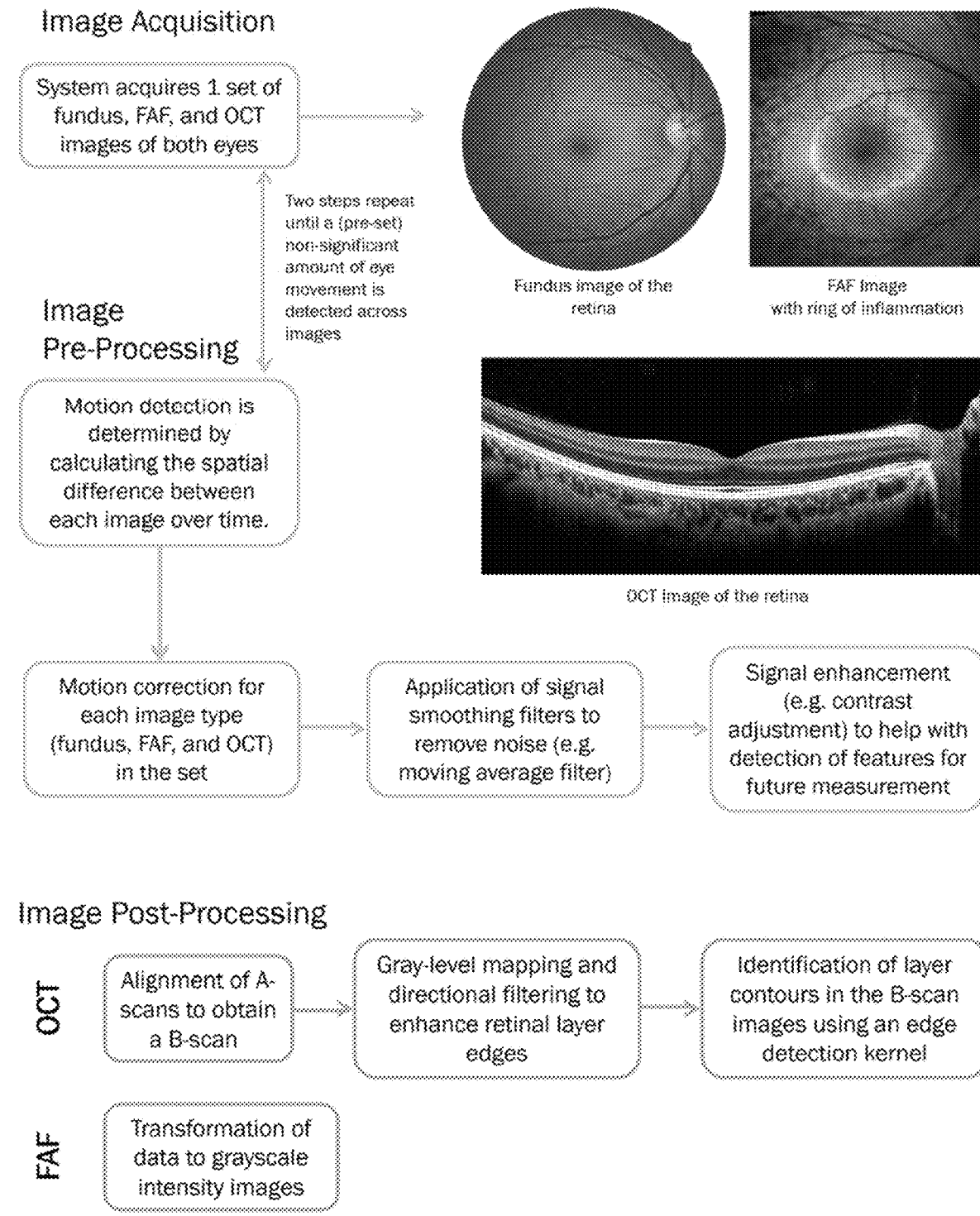
FIG. 5 summarizes steps included during image acquisition and pre- and post-processing of the image data.

FIG. 5 illustrates a set of image processing algorithms used to assess images acquired with the device. Image pre-processing (see FIG. 5) may include motion detection (where re-imaging is automatically initiated or the user is prompted to manually acquire a new image set [using the "Acquire Image" button] if excessive motion is detected), motion correction, denoising, and luminance normalization. The extent of eye motion may be determined by calculating the spatial difference between two consecutive images across the series, where a significant amount of motion, for example, can be defined as an eye movement $\geq 2.4$ μm or $\geq 2\%$ change in image signal intensities from the $1^{st}$ acquired image to the last. Pre-processing will be accomplished using an image processing algorithm that is programed into the device's signal processing unit. After image acquisition, the pre-processing algorithm can also be used to measure light levels, pupil size, and image contrast (resulting from differences in fundus opacity), and automatically incorporate these measures into the pre-processing scheme.

Post-processing (see FIG. 5) of the OCT images may include alignment of A-scans to obtain a B-scan, gray-level mapping and direction filtering to enhance retinal layer edges, and identification of layer contours in the B-scan images using an edge detection kernel. Post-processing of the FAF images may include transforming the data into grayscale intensity images. Post-processing can be accomplished using either an image processing algorithm that is programed into the device's signal processing unit or using an image processing algorithm that resides on a database cloud server.

Figure 6:
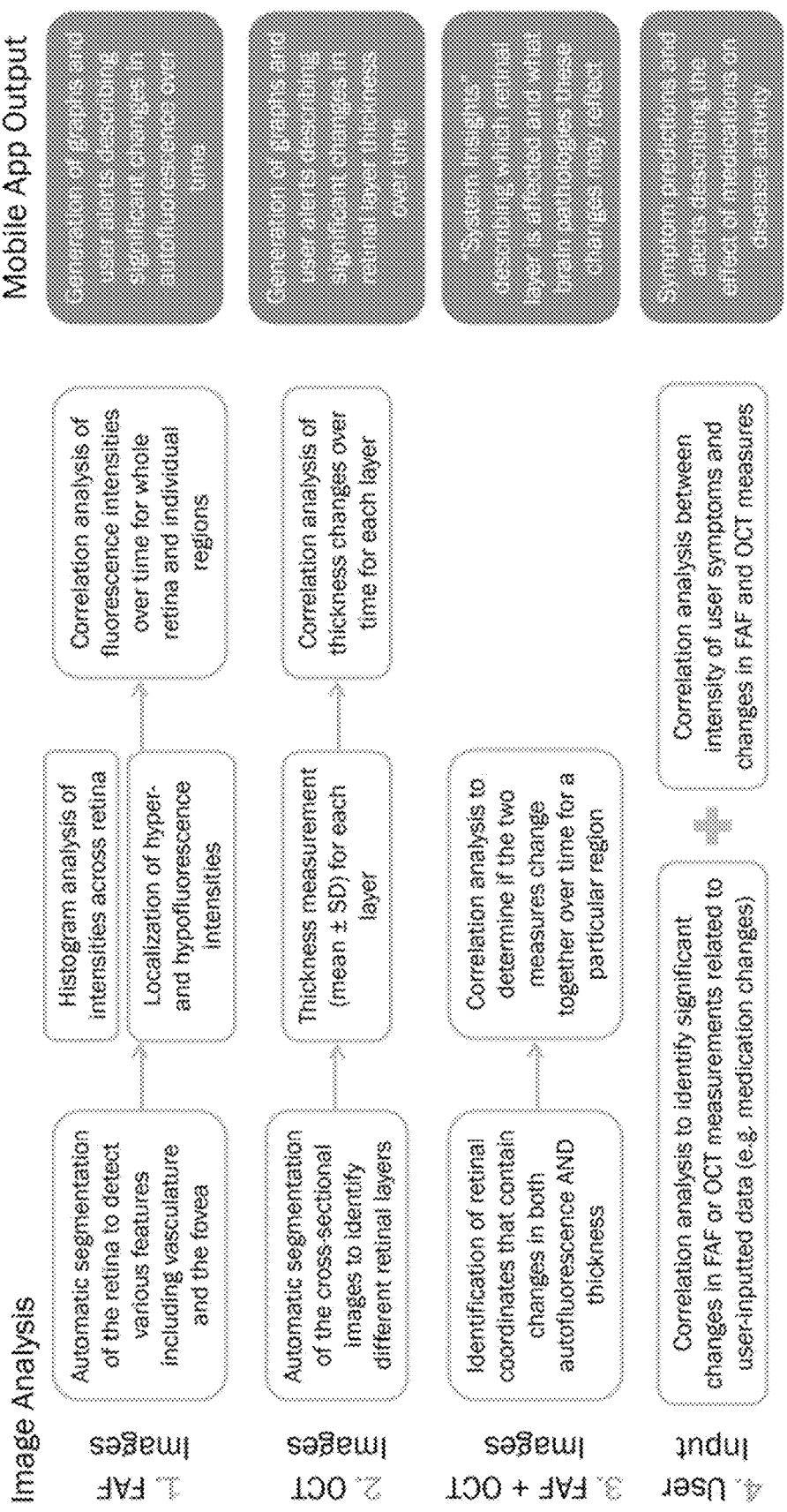
FIG. 6 illustrates an example flowchart for analysis of the FAF and OCT image data.

FIG. 6 illustrates a series of image processing algorithms used to analyze the post-processed images in order to identify significant spatial and temporal changes in the user's retinal pathology (e.g., retinal layer thicknesses and autofluorescence) over time; data analysis can be accomplished using an image processing algorithm that resides on a database cloud server.

FAF image analysis may include, but is not limited to, the following steps: automatic segmentation of the retina to detect various features including vasculature and the fovea, a histogram analysis of signal intensities across the retinal field of view (FOV), localization of hyper- and hypofluorescence intensities, and correlation analysis of signal intensities over time (e.g., by comparing results with previous acquisitions) for the whole retina and for individual regions of interest (ROIs). The resulting output to the mobile software application can include graphs of autofluorescence intensities over time and alerts describing any significant changes in autofluorescence over time.

OCT image analysis may include, but is not limited to, the following steps: automatic segmentation of the B-scan cross-sectional images to identify different retinal layers, calculation of thickness measurements for each layer, and correlation analysis of changes in thickness of each layer over time (e.g., by comparing results with previous acquisitions). The resulting output to the mobile software application can include graphs of retinal layer thicknesses over time and alerts describing any significant changes in thickness over time.

In order to localize changes in autofluorescence (e.g., representing microglial activity and inflammation, or atrophy) to specific retinal layers, a combined FAF and OCT image analysis can be conducted that may include, but is not limited to, identification of retinal coordinates for ROIs that contain changes in both autofluorescence and retinal layer thickness, and a correlation analysis to determine if the two measures change together over time for a particular region. For example, in the case where an ROI includes an increase in autofluorescence and an increase in "layer A" thickness, a conclusion may be drawn that "layer A" is experiencing an increase in inflammation. The resulting mobile software application output can include interpretations of the OCT/

FAF analysis, including which retinal layer(s) may be experiencing inflammation or degeneration, and what brain pathologies these changes may reflect.

An additional machine learning-based analysis may be used to identify significant correlations between user-inputted data (e.g., changes in symptoms and changes in medication) and changes in FAF and/or OCT measurements. The resulting mobile software application output can include symptom predictions based on changes in retinal pathology, and the effect of changes in medication on retinal pathology (e.g., disease activity).

Accompanying Mobile Software Applications

Multiple versions of the mobile software application can be used, including, but not limited to, a patient version and a clinician version.

The patient mobile app (see FIGS. 1B and 14) is for patient use and either 1) provides a summary of the user's disease activity based on the OCT and FAF measurements, 2) reminds the user to use the device and provide confirmations when images have been successfully delivered to a clinician, and/or 3) alerts the user to any changes in system status (e.g., a low device battery or recent mobile software update). The summary of disease activity can include the following information:

1. Alerts for significant changes in inflammatory activity or neurodegeneration
2. Predictions of symptom changes
3. A summary of OCT and FAF measurements in graphical display form, including any user-inputted changes in medication (e.g., date a medication was initiated, ended, or changed).

Figure 7:
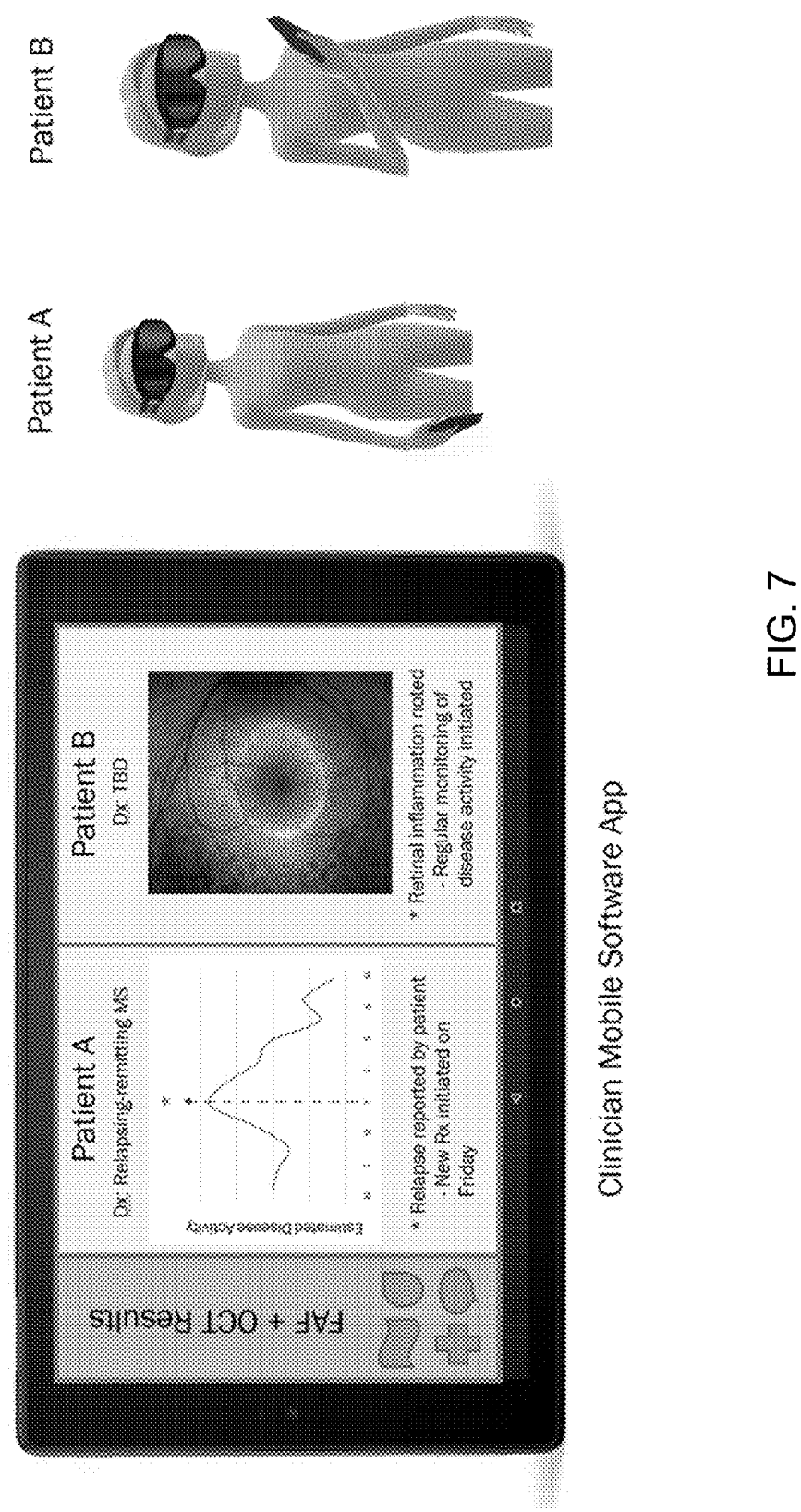
FIG. 7 illustrates the clinician mobile software application.

The clinician mobile app (see FIG. 7) can provide both raw and post-processed data, as well as analyzed results, for clinicians to use in monitoring any patient with a system; clinicians will be able to track multiple patients at once using the clinical mobile app. Similar to the patient version, it can provide automatic alerts of any significant changes in measurements acquired by a patient over time. This will enable clinicians to monitor their patients' disease activity remotely and provide an additional layer of reassurance for the patient by allowing a clinician to immediately confirm whether or not a significant change in measurements should warrant a follow-up clinical visit, change in medication, and/or additional tests.

Variations in Hardware Component Configuration

1. Headset-Only FAF-Only Configuration

Figure 8:
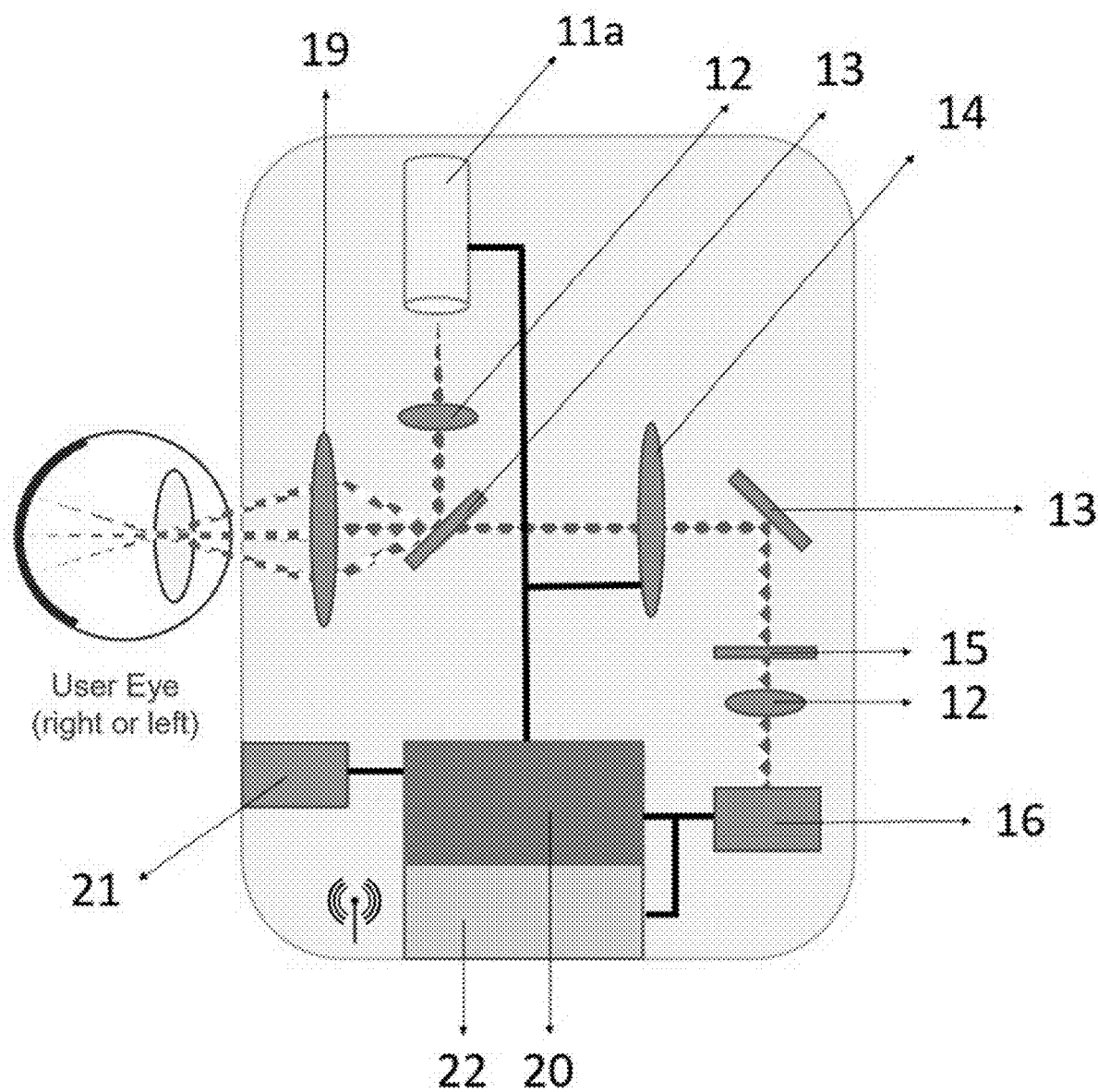
FIG. 8 illustrates a schematic view of imaging components for the headset-only, FAF-only version of an exemplary device.

FIG. 8 illustrates an FAF-only version of the device that is integrated into a headset module. Within the figure, solid lines indicate an electrical connection between the microcontroller unit and different components of the device, dashed lines indicate free light pathways, and the back of the user's eye, representing the retina, is marked by a dark arc.

Step 1. Fundus Image Acquisition: Once image acquisition is initiated manually by the user or automatically by the device, broadband light is emitted from a light source (11a), which is advantageously an LED, through an aperture (12), and directed through a lens system (19) to the user's eye using a beam splitter (13). Light reflected from the user's retina (i.e., the fundus image) then travels back through the lens and beam splitter, through an additional autofocus lens (14), and is directed through a secondary aperture (12) to a camera (16) (e.g., mini-CMOS) using a beam splitter (13). The camera then captures the fundus image and transmits it to a signal processing unit (22) for preprocessing. A microcontroller unit (20) is used to implement the fundus illumination scheme (e.g., turning the light source on for a specific amount of time and removing an emission barrier filter (15) during fundus image acquisition). A power supply (21) is used to power the microcontroller unit, which can include a battery. The emission barrier filter (15) is removed from the free-space light path using a motorized filter wheel or motorized filter flip mount (not illustrated) prior to fundus image acquisition.

Step 2. FAF Image Acquisition: Immediately after a series of fundus images are acquired, the microcontroller unit moves the emission barrier filter (15) back into the path of light. The same sequence as described above is then used to capture FAF images of the user's retina. Differences include: emitting a specific wavelength of light (e.g., 470 nm or 535-585 nm for lipofuscin excitation) from the light source (11a; or, alternatively, passing broadband light through an excitation filter immediately before or after the aperture (12) to obtain a specific wavelength) and passing the reflected light from the user's retina through the emission barrier filter (which isolates the wavelengths of light emitted from lipofuscin [e.g., 600-610 nm]) before passing through the secondary aperture (12).

A signal processing unit (22) with wireless, Bluetooth, and/or other near-field communication (NFC) capabilities is controlled by the microcontroller unit and used to pre-process the raw fundus, FAF, and OCT image data and transfer pre- and/or post-processed image data to a database server, which is advantageously a cloud server.

Figure 9A:
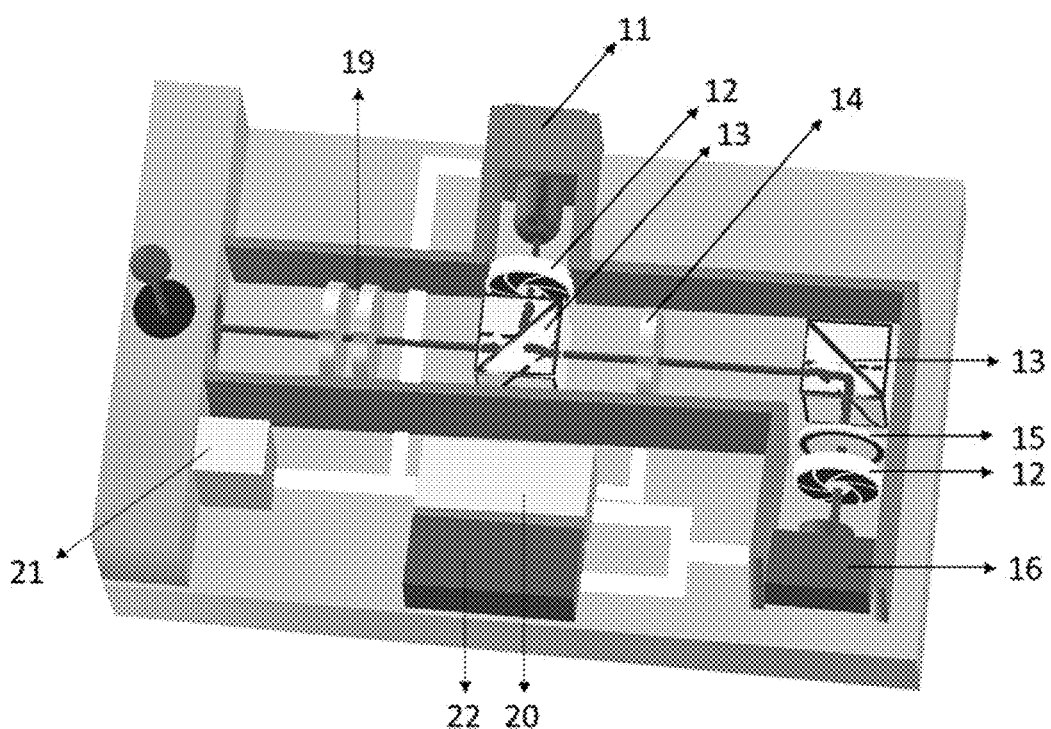
FIG. 9A illustrates a perspective view of imaging components for the headset-only, FAF-only version of an exemplary device.
Figure 9B:
FIG. 9B illustrates a perspective view of the imaging components of FIG. 9A in a headset according to the disclosure.

FIG. 9 illustrates an example 3D rendering of the FAF-only optical imaging component (see FIG. 9A) and how it is integrated into a headset (see FIG. 9B), where dark solid lines illustrate the fixation target light directed out of the device (on left) and towards the user's eye, and white lines indicate electrical connections. An additional beam splitter may be included on the left side of the device (hidden from view) in order to direct the light outward toward the user's eye. Identical versions of FAF-only imaging components are integrated into both sides of the headset goggles for consecutive scanning of both eyes (where the illustration image shows approximate scale of the hardware with-respect-to the goggles). All components are hidden from the user, such that only the fixation target light is visible to each eye.

2. Headset-Only FAF/TD-OCT Configuration

Figure 10:
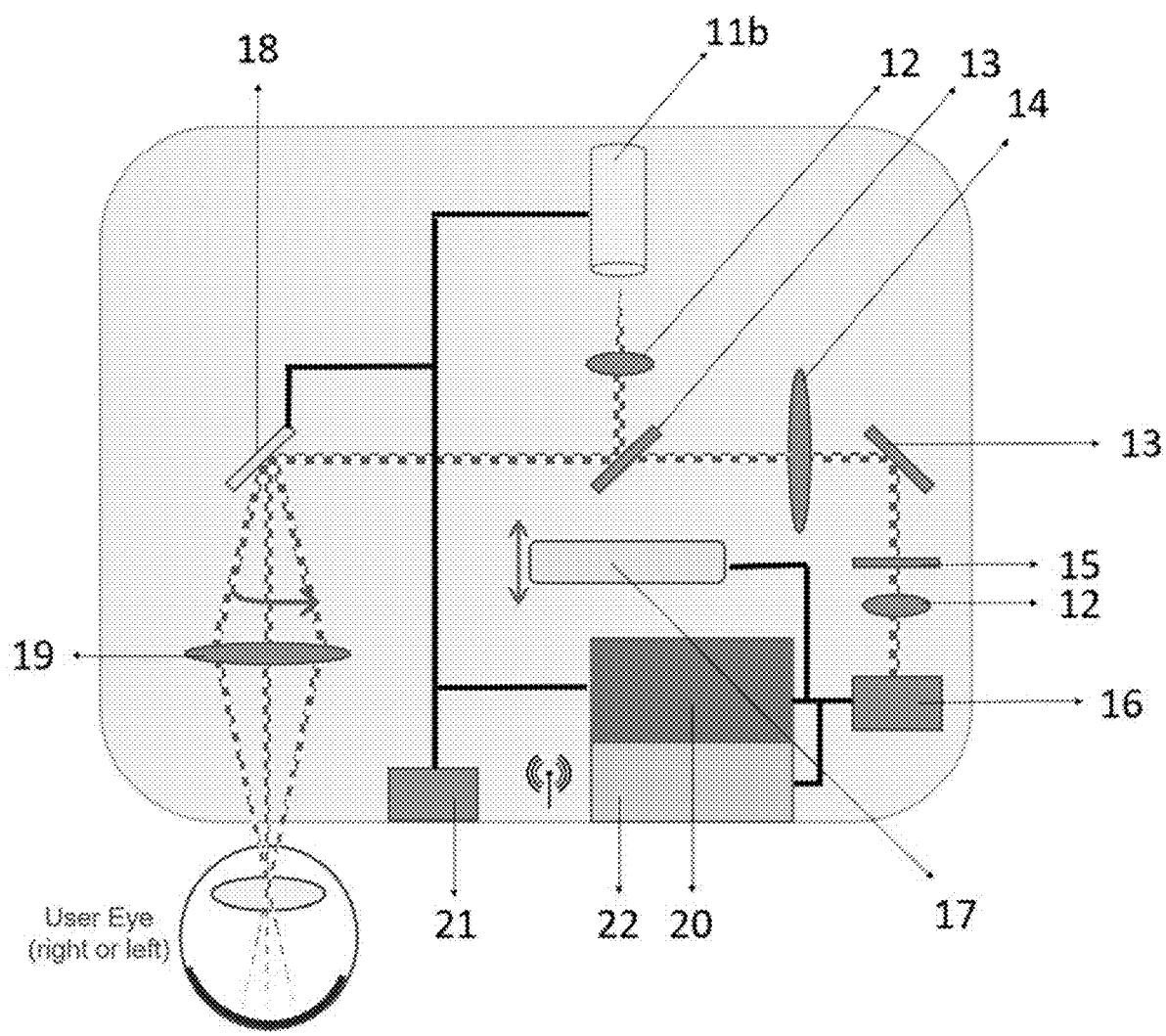
FIG. 10 illustrates a 2D schematic of imaging components for the headset-only, FAF/TD-OCT version of an exemplary device.

FIG. 10 illustrates an FAF/OCT version of the device that utilizes a time-domain form of OCT (i.e. TD-OCT) and is integrated into a headset module (identical versions of FAF-TD-OCT imaging components are integrated into both sides of the headset goggles). Arrows indicate the motion of mobile components in the device. The embodiment of FIG. 10 is similar in some respects to that of FIG. 8 and includes some similar components.

Step 1. Fundus Image Acquisition: A microcontroller is used to control a motorized MEMS scanning reference mirror (17) and motorized transverse scanning mirror (18). Prior to fundus image acquisition, the microcontroller places both mirrors in fixed positions. Fundus images are then acquired using the same sequence described for the FAF-only device.

Step 2. FAF Image Acquisition: Immediately after a series of fundus images are acquired, FAF images are acquired in the same manner as described for the FAF-only device. The scanning mirrors remain in a fixed position.

Step 3. TD-OCT Image Acquisition: Immediately after a series of FAF images are acquired, the microcontroller unit 1) positions the two scanning mirrors at their starting positions (which may or may not be different from the positions used for fundus and FAF image acquisition), and 2) removes the emission barrier filter out of the path of light. The same sequence as described for the FAF-only device is then used to capture TD-OCT images of the user's retina. Differences include: emitting a low coherence light from a superluminescent diode (11b)—this light emission is synchronized with axial scanning of the reference mirror (17) to acquire axial depth (A-scan) images, and transverse scanning of the transverse mirror (18) to combine the A-scan images into a 2D cross-sectional image (B-scan) of the whole retina. While the diode is turned on, synchronization can be achieved by using the microcontroller unit to trigger a sweep of the scanning reference mirror for every step of the transverse mirror, until a series of A-scans have been acquired across a retinal ROI. OCT scanning can be synchronized with data acquisition using a signal from the microcontroller that simultaneously triggers scanning of the mirrors and acquisition of the resulting A-scan.

3. Headset-Only FAF/SS-OCT Configuration

Figure 11:
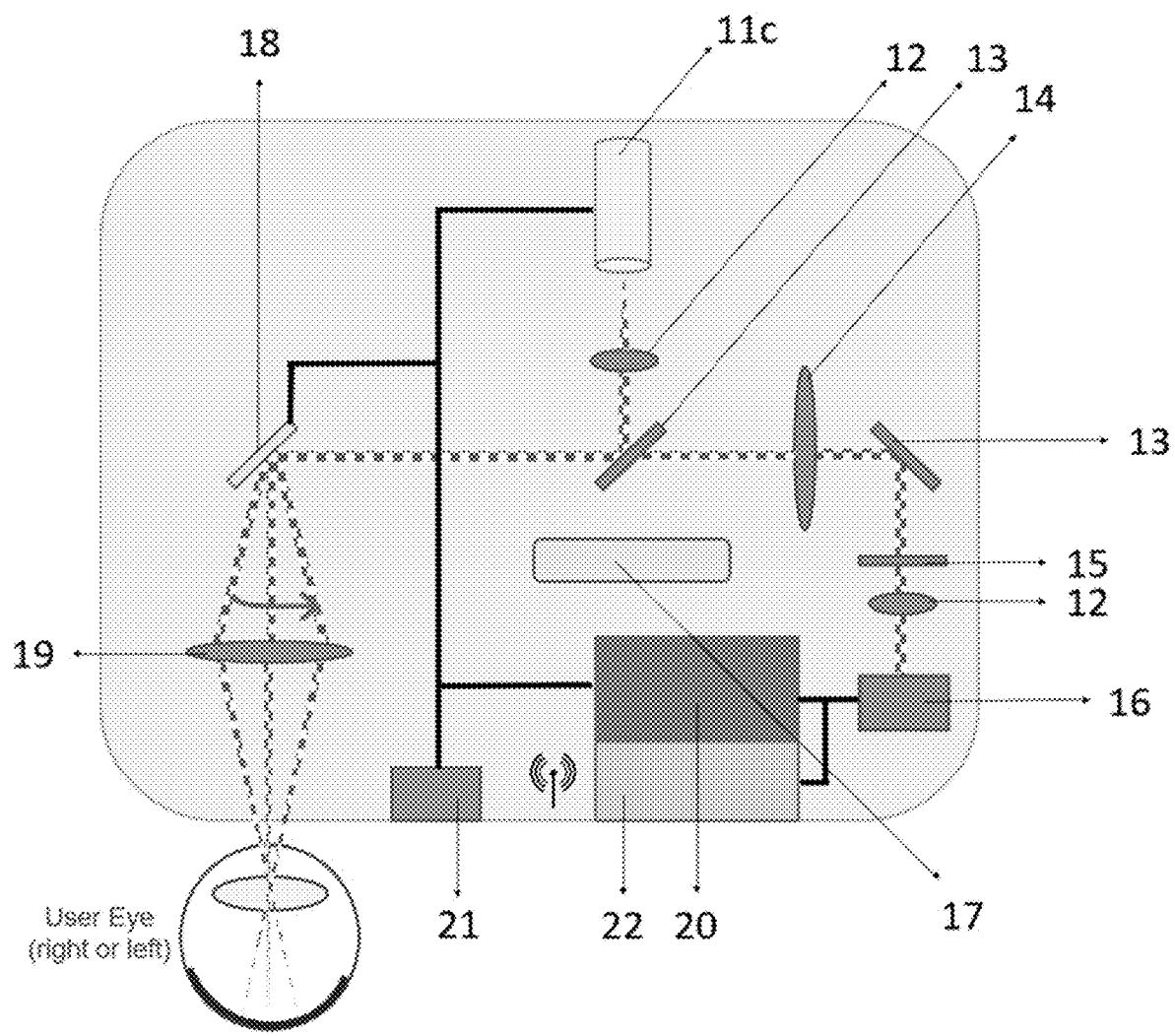
FIG. 11 illustrates a 2D schematic of imaging components for the headset-only, FAF/SS-OCT version of an exemplary device.

FIG. 11 illustrates an FAF/OCT version of the device that utilizes a swept-source form of OCT (i.e. SS-OCT) and is integrated into a headset module (identical versions of FAF-SS-OCT imaging components are integrated into both sides of the headset goggles). The embodiment of FIG. 11 is similar in some respects to that of FIGS. 8 and 10 and includes some similar components.

Step 1. Fundus Image Acquisition: Prior to fundus image acquisition, the microcontroller places the transverse scanning mirror (18) in a fixed position. Fundus images are then acquired using the same sequence described for the FAF-only device.

Step 2. FAF Image Acquisition: Immediately after a series of fundus images are acquired, FAF images are acquired in the same manner as described for the FAF-only device. The transverse scanning mirror remains in a fixed position.

Step 3. SS-OCT Image Acquisition: Immediately after a series of FAF images are acquired, the microcontroller unit 1) positions the transverse scanning mirror at its starting position (which may or may not be different from the position used for fundus and FAF image acquisition), and 2) removes the emission barrier filter out of the path of light. The same sequence as described for the TD-OCT-only device is then used to capture SS FD-OCT images of the user's retina. Differences include: emitting a narrow band of wavelengths using a tunable laser light source (11c)—this sweeping light emission is synchronized with scanning of the transverse mirror (18) to quickly acquire A-scan images, which are then combined during post-processing into a 2D cross-sectional image (B-scan) of the whole retina.

4. Headset and Tabletop SS-OCT-Only Configuration

Figure 12:
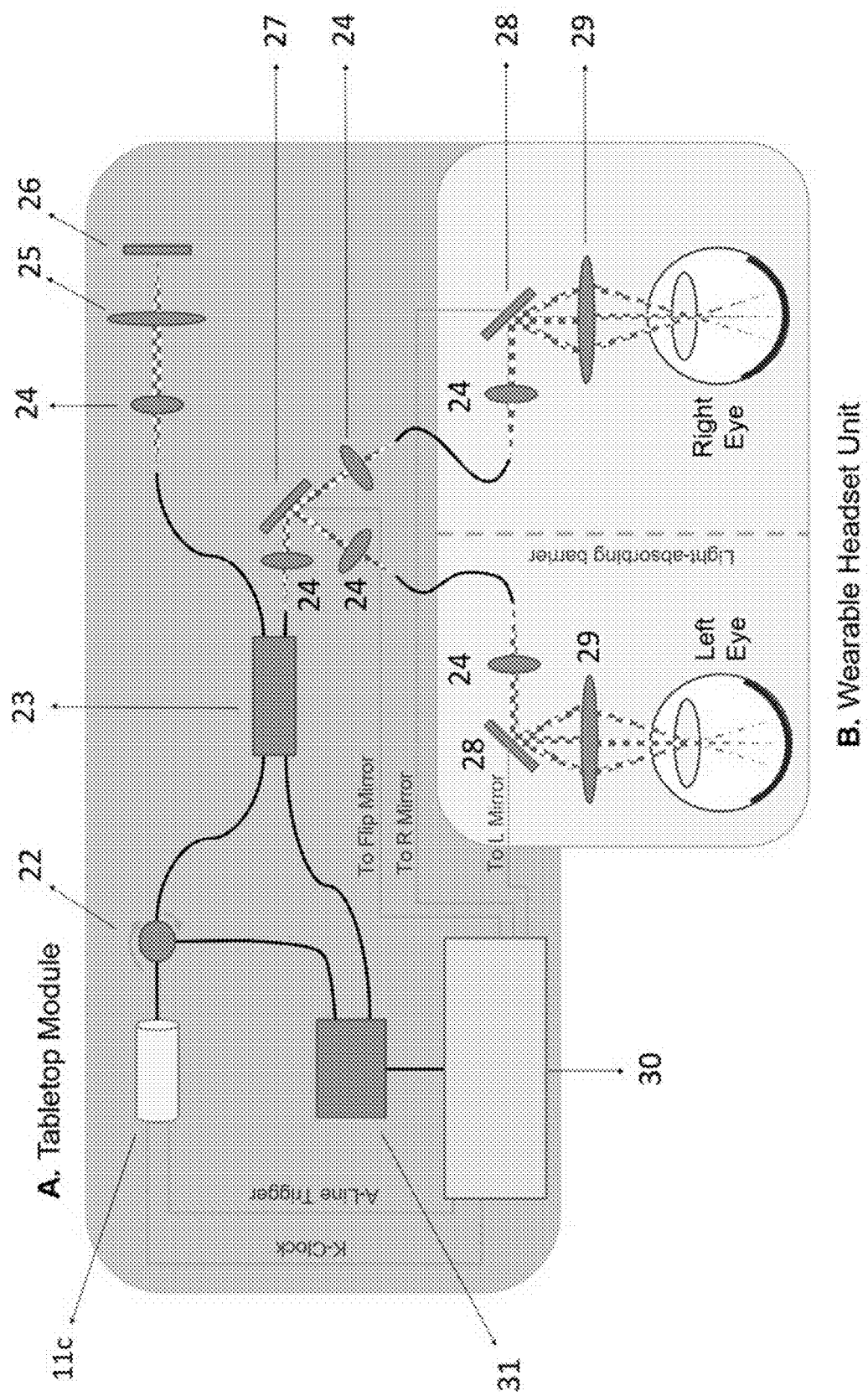
FIG. 12 illustrates a 2D schematic of imaging components for the headset and tabletop SS-OCT-only version of an exemplary device.

FIG. 12 illustrates an SS-OCT-only version of the device that is integrated into a tabletop module (A) and headset (B) (see FIG. 14), where the heaviest components are housed in the tabletop module (e.g., a 12×6×7 in box). Dashed lines indicate free light pathways, black lines indicate fiber optic cables, and thin gray lines indicate electrical connections. The SS-OCT design includes identical optical systems for each eye, which allow for consecutive scanning of both eyes within the headset unit. These components are housed in a pair of lightweight and durable goggles with adjustable straps, which can be similar to those described elsewhere herein.

The tunable laser (e.g., with 1060 nm center wavelength and 100 kHz sweep rate [i.e. 100 k A-scans/s]) (11c) delivers a spectrum of light via fiber optic cables through a circulator (22) to a 2×2 fiber coupler (23), where the beam is split and guided to 1) the reference arm (e.g., formed of a collimator (24), achromatic doublet lens (25), and static silver-coated reference mirror (26)) and 2) through a collimator to a motorized flip mirror (27). To allow for consecutive imaging of each eye, a multifunction reconfigurable I/O module with FPGA (30) is used to control the motorized flip mirror, such that the beam is directed toward the eye being imaged in the sample arm (located in the headset unit). The module is further used to control the MEMS scanning micromirrors (28) during imaging, which steer the sample beam laterally through a telecentric scan lens (29) and across each retina.

Reflected beams from the reference arm and sample arm are re-combined at the 2×2 fiber coupler and the resulting OCT signal is detected by a balanced photodetector (e.g., with a bandwidth of at least 200 MHz) (31). The OCT signal is then digitized by the multifunction module, including fast Fourier transform of the signal to obtain an A-scan. OCT scanning is synchronized with data acquisition using 1) a trigger signal from the tunable laser that triggers acquisition of the resulting axial scan (i.e. A-line), and 2) a K-clock signal from the tunable laser that will be used to trigger sampling of the OCT signal at evenly spaced optical frequencies.

5. Headset and Tabletop FAF/SS-OCT Configuration

Figure 13:
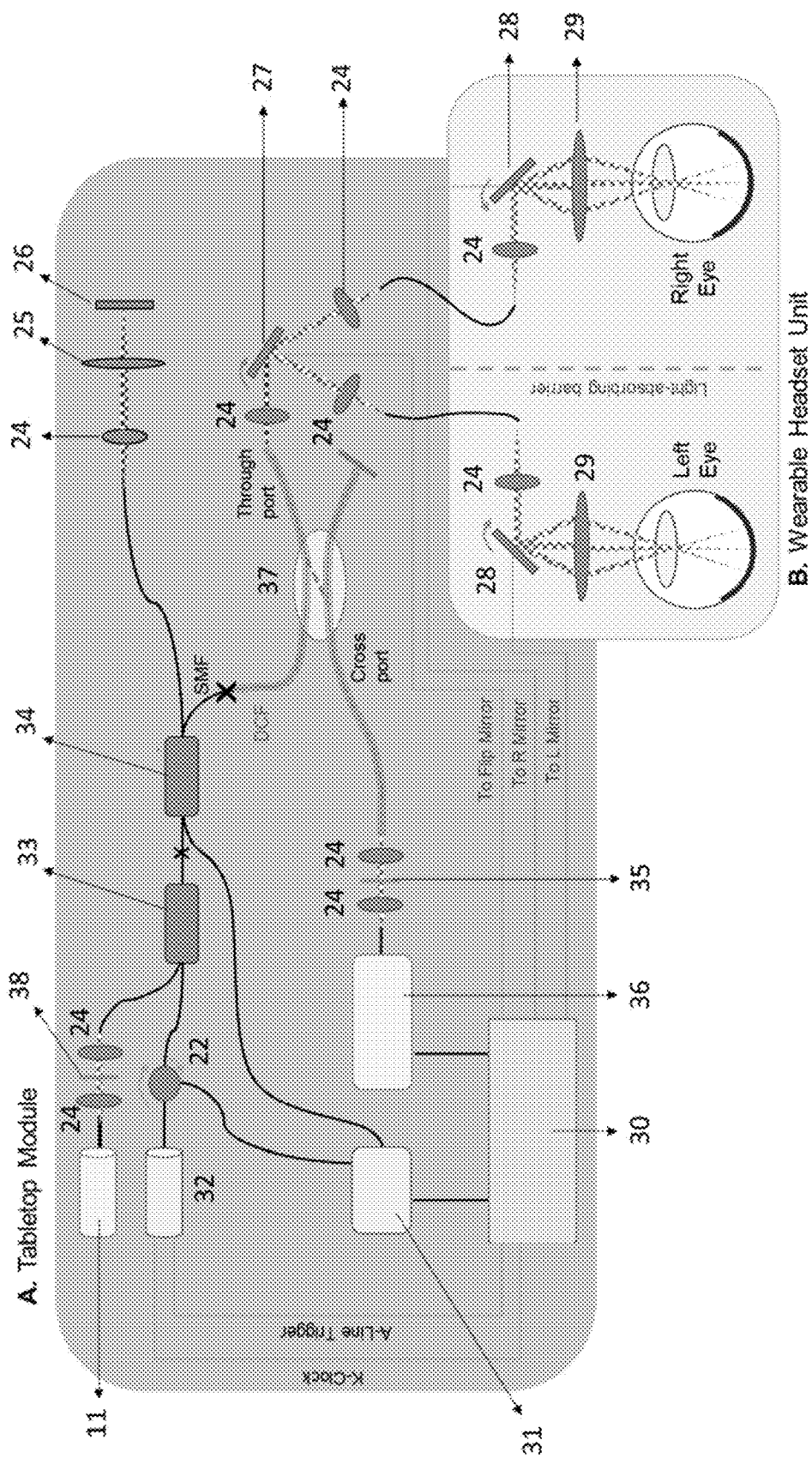
FIG. 13 illustrates a 2D schematic of imaging components for the headset and tabletop FAF/SS-OCT version of an exemplary device.

FIG. 13 illustrates an FAF/SS-OCT version of the device that is integrated into a headset and tabletop module (see FIG. 14). The heaviest SS-OCT and FAF elements are housed in the tabletop unit. Dashed lines indicate free light pathways, black lines indicate single-mode fiber (SMF) optic cables, gray double lines indicate double-cladding fiber (DCF), and thin gray lines indicate electrical connections. The embodiment of FIG. 13 is similar in some respects to that of FIG. 12 and includes some similar components.

A broadband LED and tunable laser (e.g., with 1060 nm center wavelength and 100 kHz sweep rate [i.e. 100 k A-scans/s]) can serve as the FAF and OCT light sources, respectively. Visible light from the broadband LED first travels through an excitation filter (e.g., 535-585 nm for lipofuscin excitation; 38) before being combined with near infrared (NIR) light from the tunable laser at a 2×1 wavelength division multiplexer (WMD) coupler (33) and into a SMF cable for sequential FAF and OCT imaging. These beams are then split using a 50:50 SMF coupler (34) and transmitted to the 1) reference arm (e.g., consisting of a collimator, achromatic doublet lens, and static silver-coated reference mirror) and 2) headset sample arm via the through-port of a DCF coupler (37). Use of DCF enables us to implement an all-fiber OCT/FAF system that can achieve simultaneous FAF and OCT image acquisition for each eye.

The headset includes identical optical systems consisting of a telecentric scanning lens, MEMS scanning micromirror, and collimator. To allow for consecutive imaging of each eye, the multifunction module is used to control the motorized flip mirror, such that the beams are directed toward the eye being imaged. OCT (NIR light) and FAF (visible light) beams from the tabletop unit sequentially enter either the right or left side of the headset via 1 of 2 SMF cables and are directed by a collimator to a MEMS scanning micromirror.

For OCT imaging, reflected OCT beams from both reference and sample arms are re-combined at the 50:50 SMF coupler and the resulting OCT signal is detected by a balanced photodetector (e.g., with a bandwidth of at least 200 MHz). The OCT signal is digitized by a multifunction module with FPGA, including fast Fourier transform of the signal to obtain an A-scan. OCT scanning is synchronized with data acquisition using 1) a trigger signal from the tunable laser that triggers acquisition of the resulting axial scan (i.e. A-line), and 2) a K-clock signal from the tunable laser that is used to trigger the sampling of the OCT signal at evenly spaced optical frequencies.

For FAF imaging, the reflected visible light from the sample arm is directed through the cross port of the DCF coupler and through a barrier emission filter (e.g., 615-715 nm to isolate fluorescent emissions from lipofuscin on the retina; 35). The filtered beam is then directed to a photo-multiplier light detector (36) and processed by the multifunction module.

FIGS. 15A, 15B, and 15C illustrate other exemplary embodiments, in which the headset (1) includes only a single optical imaging component (40) mounted in the headset (see FIG. 15A). In these single-component embodiments, the single optical imaging component can be mounted as illustrated in FIG. 9B and FIG. 15A, that is, for direct interaction with one of the patient's eyes, and the goggles include one or more optomechanical elements (e.g., translation stage, rails (39), driver, motor, actuator, and/or motorized wheel) in the light path so that the controller can switch the light path emanating from the single optical imaging component from being directed at the eye at which the component is mounted, to being directed at the eye at which the component is not mounted. Further optionally, other embodiments can similarly include only a single optical imaging component, but that component is not mounted as illustrated in FIG. 9B, i.e., for direct interaction with either of the patient's eyes, but instead is mounted elsewhere in the headset (see FIG. 15B). In this second set of embodiments, the goggles include a pair of sets of one or more optical elements (e.g., a galvo mirror system, additional MEMS scanning micromirror (28) and/or motorized flip mirror (27)) in the light path of the single optical imaging component, so that the controller can switch the light path emanating from the single optical imaging component to be selectively, and sequentially, directed at the left or right eye. According to yet another set of embodiments, instead of goggles which are sized and configured to fit over both eyes of a patient, a monocle-like goggle, which fits over only one eye, can be used, with a single optical imaging component mounted therein as otherwise described herein (see FIG. 15C). In this exemplary monocle (or "goggle") set of embodiments, the protocols are modified to instruct the patient to move the device from one eye, after image acquisition is complete, to the other eye, for data acquisition.

ADDITIONAL CONSIDERATIONS

In all examples of the devices and methods described herein, a safety mechanism is built-in to prevent the user from being overexposed to the light source. This may include programming the multifunction module to limit the frequency and duration of use of the light source (e.g., tunable laser) such that the device only acquires a certain number of images within a certain time frame.

In addition, spectral-domain OCT (SD-OCT) may be used in place of SS-OCT in the above configurations. This would require replacement of the tunable laser with a broadband light source and use of a spectrometer instead of a balanced photodetector.

Prior to image acquisition, each configuration of the device produces a fixation target (e.g., red light) that originates from the tunable laser in SS-OCT-only configurations, and from the broadband LED in configurations that include FAF imaging. The fixation light and audible countdown are synchronized by the microcontroller or multifunction units. The audible countdown is programed into the multifunction unit and presented using a speaker that is integrated into the headset, for which the system includes appropriate amplifiers. During fixation, the device also automatically focuses on the user's retina (e.g., using autofocus scan lenses in the sample arm that are controlled by the multifunction unit).

Eye-tracking to determine when the user's gaze is steady and ready for image acquisition is achieved using an optical tracking technique, where infrared light from the tunable laser is sent to one or both eyes in the sample arm. The reflected light from the eye is then detected by an optical sensor (e.g., the balanced photodetector) and pre-processed by the multifunction unit to determine when the user is fixating (e.g., when their gaze remains within a diameter of 1° visual angle for at least 100 ms).

In all examples, the headset includes a rechargeable battery with a USB port (FIG. 1A) and charging circuitry that powers the multifunction unit and all electrical components in the device. The tabletop unit may also include a rechargeable battery.

Example Applications

A first application of the systems and methods described herein will be to multiple sclerosis (MS) patients.

MS is a debilitating chronic inflammatory disease in which the body's immune system attacks the protective myelin sheath surrounding nerve fibers, causing damage to the central nervous system (CNS)—including the retina. This recurring inflammatory response and neurodegeneration produces symptom relapses and long-term disability, including weakness, pain, spasms, and cognitive disability. MS affects nearly 1 million people in the US and more than 2.5 million people worldwide, with most individuals being diagnosed between 20-40 years old. 85% of MS patients are diagnosed with a relapsing-remitting form of the disease (RRMS). RRMS is characterized by unpredictable and transient MS attacks: the appearance of active inflammatory lesions and scar tissue (sclerosis) within the CNS that may be asymptomatic or accompanied by highly variable symptoms. Without effective treatment, the majority of RRMS patients ultimately transition to secondary-progressive MS (SPMS), with symptoms worsening more steadily over time, and for which there are currently no FDA-approved therapies.

Early detection of disease activity and proper treatment of RRMS is crucial to reducing the risk of disease progression and accrual of disability. Current practice relies on 1-2 annual clinical visits and magnetic resonance imaging (MRI) of the CNS to assess changes in disease activity and the efficacy of a patient's treatment regimen. However—other than patient reporting of symptoms—there is currently no way to monitor MS between these periodic visits, increasing the likelihood that new untreated inflammatory activity in the CNS results in permanent neuronal damage. This is especially true of the 80-90% of new lesions that are asymptomatic and result from subclinical disease activity. Since symptomatic relapses vary in type, length, and severity, patients do not always recognize and report an MS exacerbation (attack), further hampering a physician's ability to intervene in a timely manner. The resulting delay in treating MS activity in RRMS patients has been shown to have a negative impact on MS prognosis, including a decline in quality of life and functional ability.

The systems and methods described herein can improve clinical practice by addressing the critical unmet need for more effective and frequent MS monitoring. Information captured by the device provides patients and physicians alike with an objective means of tracking disease activity. This in turn helps patients identify MS disease processes (including inflammatory activity) and encourage them to immediately report these to their physician, and/or the data is automatically reported to the clinician. Clinicians in turn use the measurements to help determine if a treatment is effective based on retinal changes that occur between clinical visits, and/or if additional or new therapy, including but not limited to medication (e.g., a steroid course, change in amount and/or type of medication, and combinations thereof). The result is earlier detection of MS activity and more efficient monitoring of treatment efficacy, leading to shorter-term use of ineffective drugs and likely a further reduction in risk of disease progression due to earlier intervention. Specifically, use of the device is beneficial to individuals with clinically isolated syndrome (CIS) who have not yet been diagnosed with MS, newly diagnosed MS patients, individuals experiencing a relapse, and patients with a recent change in treatment regimen.

In an alternative embodiment, the systems and methods can also be applied to patient groups with any condition that presents in the retina. Example target markets include:

Neuroinflammatory Diseases. Data gathered and/or produced by the systems and methods described herein may be used to monitor any neurological disease that is characterized by an inflammatory reaction in the central nervous system and manifests (structurally and/or functionally) in the retina. This may include (but is not limited to) the following diseases: Multiple Sclerosis (MS), Parkinson's disease, Alzheimer's disease, Acute disseminated encephalomyelitis (ADEM), Optic Neuritis (ON), Transverse Myelitis, and Neuromyelitis Optica (NMO).

Neurodegenerative Diseases. Data gathered and/or produced by the systems and methods described herein may be used to monitor any neurological disease that is characterized by an atrophy of the central nervous system and manifests (structurally and/or functionally) in the retina. This may include (but is not limited to) the following diseases: Dementias, Prion disease, Motor neuron diseases (MND), Huntington's disease (HD), Spinocerebellar ataxia (SCA), Spinal muscular atrophy (SMA), and Amyotrophic lateral sclerosis (ALS).

Retinal Inflammatory Diseases. These include (but are not limited to) age-related macular degeneration (AMD), diabetic retinopathy (DR), and glaucoma. Symptoms and pathology for these diseases are directly related to changes in retinal inflammation, such that the systems and methods described herein can be used to help patients monitor their conditions and response to treatment at home.

Research Groups. Data gathered and/or produced by the systems and methods described herein may be used as an additional outcome measure during studies of retinal, neurodegenerative, or other diseases. Since the device can be used in subjects' homes, groups can gather a greater depth of temporal data describing patient treatment responses, including in rural and developing country sites with limited access to retinal and/or brain imaging equipment. In some cases, the device will help lower study costs by requiring fewer site visits if similar data can be acquired with the system in a patient's home. There are currently more than 3,600 open clinical trials for retinal and cortical neurodegenerative diseases worldwide led by pharmaceutical companies and research institutions.

Traumatic Brainy Injury. Neuroinflammation is a major cause of behavioral and eye/brain pathological changes following TBI (including concussion). The systems and methods described herein can be used by patients at home and by military in the field.

Epilepsy. Studies have demonstrated that neuroinflammation initiates seizures and that this immune response can be detected in the retina. Monitoring is crucial to epilepsy patients with recurring seizures.

Addiction. Neuroinflammatory responses are a known consequence of drug and alcohol abuse. Monitoring of inflammation can help track patient responses to treatment and help determine patient risk of relapse post-treatment.

In addition, the systems and methods described herein can be used by otherwise healthy individuals to monitor their brain health at home as a preventative measure, particularly among the elderly. In this case, the system may be used as described or with the following change: instead of automatic data transfer to a clinician, the user may instead be alerted when significant changes in retinal structure or function have been detected that should be shared with a clinician. The user can then use their mobile software app to export and/or share processed data and analyzed results with their doctor.

Example Protocol for Use by a Patient (see FIG. 14)

The following is an exemplary protocol of how the systems and devices described herein can be used by a patient at home, as well as by their physician during clinical visits. This example does not include use of an optional virtual reality option.

Daily Use at Home: Image Acquisition

Figure 1B:
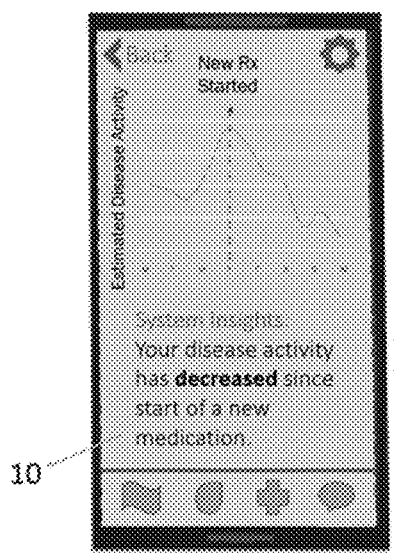
FIG. 1B illustrates a patient mobile app according to an exemplary embodiment of the disclosure.
Figure 1C:
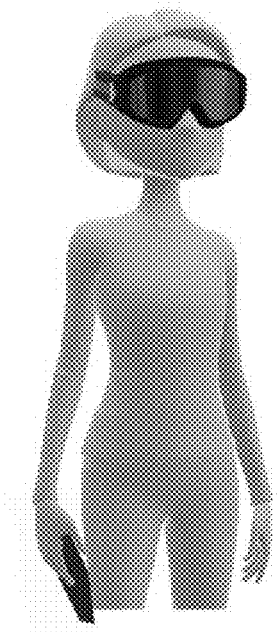
FIG. 1C illustrates a patient wearing the headset-only version of the system of FIG. 1A.

Each morning, the patient will place the goggles on their head such that the strap is comfortably adjusted to their head size and little-to-no light is escaping past the black goggle shield (FIGS. 1C and 14).

The patient will turn the device on using the power button on the side of the goggles (FIG. 1A).

An audible countdown from "ten" to "one" will commence while the patients' eyes naturally dilate as they adjust to the darkness of the headset (where dilated eyes will enable the camera to see and capture better images of the retina).

At the end of 10 seconds, a red fixation light (originating from the system's light source) will turn on in the goggles for the patient to fixate on (in order to reduce any eye movements that could interfere with clear image acquisition).

If the device is in automatic mode, the device will automatically acquire fundus, FAF, and/or OCT images once it detects a steady gaze, as identified by the multifunction module, signal processing unit, or cloud-based image processing software.

If the device is in manual mode, the patient will press the acquisition button on the side of the device once he/she is ready for the device to capture images (i.e., they are ready to hold their gaze steady for a few seconds).

Immediately prior to image acquisition in both cases, the red lights advantageously, although optionally, blink one or more times to warn the patient that the device will soon capture images and to keep their gaze as steady as possible.

After the images have been captured, all lights in the device will turn off, leaving the patient in a brief darkness.

The device's multifunction unit (or signal processing unit, or cloud-based image processing software) will immediately calculate the amount of eye movement across the series of images (e.g., by calculating the signal intensity difference between two consecutive images across the series, where a significant amount of motion is indicated by a significant change in pixel locations or change in image signal intensities from the $1^{st}$ acquired image to the last).

If a significant amount of motion is detected, the device will turn the red fixation light back on and/or give a verbal cue to indicate that image acquisition was not successful and that the images need to be re-acquired. The patient will then repeat the process.

If a non-significant amount of motion is detected, the device will turn a green light on and/or give a verbal cue to indicate that image acquisition was successful.

Once the patient receives a green light, they will remove the goggles and turn off the device using the power button. Alternatively, the device will turn off by itself following a period of non-use.

This entire process should last no more than five minutes, however shorter or longer times can also be used.

Daily Use at Home: Syncing with the Mobile App and Inputting User Data

Immediately after image acquisition or later the same day, the patient will turn on the device using the power button and open the app on their computing, e.g., PC or mobile, device. If the device is in range and on, the mobile app will automatically sync with the device. This syncing process will include: wireless transfer of the pre-processed and/or post-processed image data to a database cloud server, analysis of the images, and transfer of the results (including graph updates) to the mobile app.

Once syncing is complete, the patient is preferably guided through a series of app pages that helps the patient to easily report the location and intensity of any new symptoms or changes in existing ones.

In addition, the patient can input any changes in medications and/or supplements, as well as the dates of any recent clinical visits.

The patient mobile app can then provide simple text to help the patient understand the significance of their results, including:

Trends over time (for example, in the case of an increase in autofluorescence intensity over time following a change in prescription, the app may say "Your disease activity has increased since you started your new medication. You may want to contact your doctor to determine if your prescription should be changed").

Alerts to any significant changes in disease activity (for example, "Your inflammation has been steadily decreasing—you may be entering a period of MS remission").

Predictions based on historical trends (calculated by the software on the database cloud server) between the patient's retinal measurements and inputted symptoms (for example, "Your disease activity has been increasing over the past 2 weeks. Based on your past trends, you may experience a symptom exacerbation soon").

Physician Use at the Clinic: Transmission of Data to a Clinician

After the patient has finished inputting any additional relevant data, the results from their data acquisition will be automatically sent to their clinician for remote review.

The patient will be notified when the transmission has been received by the clinician.

The clinician will then be able to view the following information about their patient using the clinician mobile software app:

Changes in autofluorescence over Y period of time—this may be labeled as "Estimated Brain Inflammation or Atrophy from FAF"

Changes in retinal thicknesses over Y period of time—this may be labeled as "Estimated Brain Inflammation or Atrophy from OCT"

Estimated changes in autofluorescence for specific retinal layers over Y period of time—this may be labeled as "Estimated Brain Inflammation or Atrophy from FAF+OCT"

These graphs will also include any prescription compliance-related data added by the patient.

Based on the results received, the physician will determine if any changes in retinal pathology warrant a change in treatment regimen or follow-up visit. Additionally, the physician can prescribe one or more therapies including, but not limited to medications, including but not limited to steroids, vitamins, immunosuppressives, and anti-inflammatory drugs, and the patient then takes those therapies; alternatively, the physician can instruct the patient to stop one or more therapies the patient is currently taking; or combinations of these two. Thereafter, the patient again uses the systems and methods as described herein at a later time, and the physician can assess the efficacy of that new regimen; this cycle can be repeated.

Device Hardware Specifications

Device Packaging (FIGS. 1A and C, FIG. 14): exemplary devices can have one or more of the following attributes.

A device that is portable and can be used by the patient at home and while traveling A device with packaging that includes a headset that fits the majority of faces, for comfort and ease-of-use by the user A device with lightweight packaging A device with durable and ruggedized packaging (including to withstand fluctuations in acceleration, temperature, humidity, and shock)

A device with custom headset packaging that reduces or eliminates outside light to allow the user's pupils to naturally dilate, thus enhancing the quality of images acquired by the device A device with packaging that provides a target for the user to easily fixate on while operating the device (to help reduce significant eye movements during image acquisition)

A device with packaging that conceals all image acquisition and processing components from the user A device with buttons to activate the system that are easily distinguished by touch A device with buttons that allow the user to choose either manual or automatic image acquisition A device with voice commands that guides the user through the image acquisition process and use of the device A device with a rechargeable battery A device with built-in safety measures to prevent overuse and overexposure of the user to the light source(s), such as automatically turning the device off after some time of not being used Device Image Acquisition: exemplary devices can have one or more of the following attributes.

A device that captures fundus images of the retina

A device that captures FAF images of the retina, including images of regions with hyperfluorescence and hypofluorescence A device that captures OCT images, including cross-sectional images of the retina to measure layer thicknesses A device that captures only FAF images, only OCT images, or both OCT will be implemented either in the time-domain (TD-OCT, FIG. 10) or Fourier-domain (FD-OCT, FIGS. 11-13)

A device that is able to acquire fundus, FAF, and OCT images in quick succession or simultaneously A device that can capture images in undilated (non-mydriatic) eyes A device that can automatically detect when the user is fixating A device that is able to automatically focus on the user's retina as the user fixates on a target A device that can also measure other relevant information about the user's eye, including light levels in the headset, pupil size, and fundus opacity (i.e. image contrast)

A device that uses a light source that is safe for use in humans, according to ISO and ANSI standards for light safety A device that acquires image data in a common image format (e.g., DICOM)

Image Processing (FIGS. 5B-C): exemplary systems can have one or more of the following attributes.

A system (defined as the device, a cloud server, a mobile software application, or combinations thereof) that temporarily stores the resulting raw fundus, FAF, and OCT images A system that uses signal and image processing algorithms to pre-process the raw image data, including: motion detection and correction, signal filtering to remove noise, signal enhancement (including image contrast adjustment and luminance normalization)

A device that is able to detect when images contain a significant amount of motion and are not interpretable (for example, using an eye-tracking algorithm)

A device that notifies the user to re-acquire the images if significant motion is detected A device that is able to (e.g., wirelessly) transmit the pre-processed image data to a cloud server or mobile software application Image Data Analysis (FIG. 6): exemplary systems can have one or more of the following attributes.

A system that wirelessly transmits pre-processed images from the device to a cloud server and/or mobile software application A system that contains an image post-processing and analysis algorithm that extracts the following FAF and OCT measures, respectively:

Quantification of hyper- or hypofluorescent intensities across the user's retina, including the coordinate location of intensities above or below a specified threshold Quantification of retinal layer thicknesses across the retina, including the coordinate location of thicknesses above or below a specified threshold A system that combines FAF and OCT measures to provide an estimate of which retinal layers are experiencing a change in autofluorescence (i.e., inflammation or atrophy)

A system that automatically co-registers images of the retina from multiple acquisition sessions (for comparison of FAF and OCT measures over time)

A system that generates graphs of FAF, OCT, and FAF+OCT measures over time, including—changes in autofluorescence intensity, changes in retinal layer thicknesses, changes in estimated autofluorescence intensity for each retinal layer A mobile app that automatically updates the above graphs each time new image data is acquired and analyzed A mobile app that identifies changes in FAF and OCT measures that are significantly related to user-inputted data (such as time since a medication was changed)

Mobile Software Specifications (for the clinician and/or patient mobile apps): exemplary devices can have one or more of the following attributes.

Example patient (FIGS. 1B and 14) and clinician (FIG. 7) mobile software application user interfaces A mobile app that includes a user-friendly interface A mobile app that saves X amount of analysis results for Y days depending on the user's chosen subscription plan A mobile app that provides users with raw, pre-, and post-processed fundus, FAF, and OCT images of the retina (acquired within Y days)

A mobile app that provides users with a graphical illustration of changes in FAF and OCT measures over time A mobile app that allows users to easily input information that can be tracked alongside any significant changes in FAF and OCT measures, including: date when a new medication is started, date when a medication is stopped or dosage changed, onset of a new symptom, date when a symptom increases or decreases in intensity/severity, and date of last clinical visit A mobile app that alerts the user to any changes in FAF and OCT measures (i.e., disease activity)

A mobile app that provides symptom predictions to the user based on changes in FAF and/or OCT measures A mobile app that includes a community discussion board for any device, app, or health-related questions A mobile app that provides patients with reminders to use the device regularly A mobile app that notifies the user when data has been successfully transmitted or received A system that allows remote monitoring of retinal pathology and associated neurological disease A system that can provide both functional and structural assessment of the retina In yet further embodiments, the applications describes as being executed on mobile devices can instead be implemented to be displayed via a web browser running on a general purpose computing device, e.g., as web content which is accessed by the patient, the clinician, or both over the internet.

Computing devices, including mobile devices and/or servers, described herein can include one or more of a display device, a keyboard, a pointing device, a network connection, processor, video adapter, system memory, network interface, serial port interface that are communicatively linked together by a system bus. The system memory can include read only memory (ROM) and random access memory 3226. A basic input/output system (BIOS) is stored in ROM. The BIOS can contain basic routines that help to transfer information between elements/subsystems within the computer during certain computer operations. A number of program modules, components, and/or engines can be temporarily stored in the RAM, such as an operating system, a component control engine, and a component database. Permanent storage for the program modules, components, and/or engines described herein can be provided by one or more types of storage media interfaced to the computer including, but not limited to, a hard disk drive, an optical disk drive, magnetic disk drive, flash memory cards, etc. In another embodiment, permanent storage for the program modules, components, and/or engines can be provided by one or more distributed computing devices (e.g., application servers, database servers, etc.) that are communicatively connected to the computer via a network connection.

REFERENCES

1 Saidha S, Sotirchos E S, Oh J, et al. (2013) "Retinal axonal and neuronal measures in multiple sclerosis reflect global CNS pathology." JAMA Neurol. 70(1):34-43.

2 Ahl M, Avdic U, Skoug C, et al. (2016) "Immune response in the eye following epileptic seizures." J. Neuroinflammation. 13:155.

3 Xu L, Nguyen J V, Lehar M, et al. (2016) "Repetitive mild traumatic brain injury with impact acceleration in the mouse: Multifocal axonopathy, neuroinflammation, and neurodegeneration in the visual system." Exp. Neurol. 275:436-449.

4 Wang N K, Fine H F, Chang S, Chou C L, Cella W, Tosi J, et al. Cellular origin of fundus autofluorescence in patients and mice with a defective NR2E3 gene. Br J Ophthalmol. 2009; 93(9):1234-40.
5 Brar M, Kozak I, Cheng L, Bartsch D U, Yuson R, Nigam N, et al. Correlation between spectral-domain optical coherence tomography and fundus autofluorescence at the margins of geographic atrophy. Am J Ophthalmol. 2009; 148(3):439-44.
6 Chung H, Park B, Shin H J, Kim H C. Correlation of fundus autofluorescence with spectral-domain optical coherence tomography and vision in diabetic macular edema. Ophthalmology. 2012; 119(5):1056-65.
7 Cirrus photo. Carl Zeiss Meditec, Inc. Cited Dec. 2, 2017. Available from: https://www.zeiss.com/meditec/us/products/ophthalmology-optometry/glaucoma/diagnostics/fundus-imaging/cirrus-photo.html#more-information.
8 Spectralis. Heidelberg Engineering Inc. Cited May 5, 2018. Available from: https://business-lounge.heidelbergengineering.com/us/en/products/spectralis/.
9 3D OCT-2000 FA plus. Topcon. Cited Dec. 2, 2017. Available from: http://www.topcon.co.jp/en/eyecare/products/product/diagnostic/oct/3DOCT-2000_E.html.
10 D-EYE Portable Retinal Imaging System. D-EYE Srl. Cited Aug. 31, 2017. Available from: https://www.d-eyecare.com/en_US#vision.
11 Pictor Plus Ophthalmic Camera. Volk Optical, Inc. Cited Dec. 2, 2017. Available from: https://volk.com/index.php/volk-products/ophthalmic-cameras/volk-pictor-plus-digital-ophthalmic-imager.html.
12 Visuscout 100 Handheld Fundus Camera. Carl Zeiss Meditec, Inc. Cited Dec. 2, 2017. Available from: https://www.zeiss.com/meditec/us/products/ophthalmology-optometry/essential-line-basic-diagnostics/iop-and-retina-screening/visuscout-100.html.
13 The Horus Scope. Jedmed. Cited Dec. 2, 2017. Available from: https://www.jedmed.com/products/portable-fundus-camera.
14 Envisu C2300. Leica Microsystems. Cited Aug. 31, 2017. Available from: http://www.leica-microsystems.com/products/optical-coherence-tomography-oct/details/product/envisu-c-class/.
15 iScan. Optovue, Inc. Cited Dec. 2, 2017. Available from: http://www.optovue.com/products/iscan/.
16 Vinekar A, Sivakumar M, Shetty R, Mahendradas P, Krishnan N, Mallipatna A, et al. A novel technique using spectral-domain optical coherence tomography (Spectralis, SD-OCT+HRA) to image supine non-anaesthetized infants: utility demonstrated in aggressive posterior retinopathy of prematurity. Eye (Lond). 2010; 24(2):379-82.
17 Tao Y K, Ehlers J P, Toth C A, Izatt J A. Intraoperative spectral domain optical coherence tomography for vitreoretinal surgery. Opt Lett. 2010; 35(20):3315-7.
18 Ehlers J P, Tao Y K, Farsiu S, Maldonado R, Izatt J A, Toth C A. Integration of a spectral domain optical coherence tomography system into a surgical microscope for intraoperative imaging. Invest Ophthalmol Vis Sci. 2011; 52(6):3153-9.
19 Lu C D, Kraus M F, Potsaid B, Liu J J, Choi W, Jayaraman V, et al. Handheld ultrahigh speed swept source optical coherence tomography instrument using a MEMS scanning mirror. Biomed Opt Express. 2013; 5(1):293-311.
20 Kim S, Crose M, Eldridge W J, Cox B, Brown W J, Wax A. Design and implementation of a low-cost portable OCT system. Biomed Opt Express. 2018; 9(3):1232-1243.

While the devices, systems, and methods of the present disclosure have been described in detail with reference to exemplary embodiments thereof, it will be apparent to one skilled in the art that various changes can be made, and equivalents employed, without departing from the scope of the invention. The foregoing description of the exemplary embodiments of the devices, methods, and systems has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the devices, systems, and methods and practical applications of the same to enable one skilled in the art to utilize the disclosed devices, systems, and methods in various embodiments as are suited to the particular use contemplated. It is intended that the scope of the present disclosure be defined by the claims appended hereto, and their equivalents. The entirety of each of the aforementioned documents is incorporated by reference herein.

That which is claimed is:

1. A system useful for FAF and OCT image acquisition of a patient's eye, the system comprising:
   a broadband LED as an FAF light source;
   a tunable laser as an OCT light source;
   a 2×1 wavelength division multiplexer coupler;
   a first lightpath communicating visible light from the broadband LED, the first lightpath including an excitation filter, the first lightpath communicating light from the excitation filter to the coupler;
   a single-mode fiber receiving light from said coupler;
   a second lightpath communicating near infrared light from said tunable laser to said coupler, wherein the coupler combines light from said first and second lightpaths into the single-mode fiber for sequential FAF and OCT imaging;
   a splitter receiving light from said single-mode fiber;
   third and fourth lightpaths receiving light from said splitter;
   a reference arm in said third lightpath; and
   a headset sample arm in said fourth lightpath.

2. The system according to claim 1, wherein the broadband LED has a 1060 nm center wavelength and the tunable laser has a 100 kHz sweep rate.

3. The system according to claim 1, wherein the excitation filter operates at 535-585 nm.

4. The system according to claim 1, wherein said reference arm comprises a collimator, achromatic doublet lens, and static silver-coated reference mirror.

5. The system according to claim 1, wherein splitting and transmitting light is performed via a through-port of a double-cladding fiber coupler.

6. A process of FAF and OCT image acquisition of a patient's eye, the process comprising:
   generating light with a broadband LED and tunable laser, wherein visible light from the broadband LED first travels through a lipofuscin excitation filter;
   combining light from said lipofuscin excitation filter with near infrared light from said tunable laser; and
   splitting and transmitting light from said combining step to
      a reference arm, and
      a headset sample arm configured to be positioned in front of a patient's eye,
   wherein said splitting and transmitting light is performed via a through-port of a double-cladding fiber coupler.

7. The process according to claim 6, further comprising: simultaneously acquiring FAF and OCT images of said patient's eye.

8. The A process according to claim 6, wherein the broadband LED has a 1060 nm center wavelength and the tunable laser has a 100 kHz sweep rate.

9. The process according to claim 6, wherein the lipofuscin excitation filter operates at 535-585 nm.

10. The process according to claim 6, wherein said combining comprises combining at a 2×1 wavelength division multiplexer coupler and into a single-mode fiber for sequential FAF and OCT imaging.

11. The process according to claim 6, wherein said reference arm comprises a collimator, achromatic doublet lens, and static silver-coated reference mirror.

12. A system for fluorescence and OCT image acquisition of a patient's eye, the system comprising:
  a FAF light source;
  an OCT light source;
  a 2×1 wavelength division multiplexer, combining light from the FAF light source and light from the OCT light source and directing it to a splitter; and
  a splitter receiving light from said wavelength division multiplexer and directing to a reference arm and a double-cladding fiber coupler;
  said double-cladding fiber coupler, with a first port connected to said splitter, a second port connect to a sample arm, and a third port connected to a detector for FAF imaging, and
  said sample arm comprising a headset, enabling light scanning of a patient's eye for both FAF and OCT imaging.

13. The system according to claim 12 where the OCT light source is a tunable laser.

14. The system according to claim 12 where the OCT light source is a superluminescent diode.

15. The system according to claim 12, wherein the OCT light source has a center wavelength between 1040 nm and 1060 nm center wavelength, and a sweep rate greater than or equal to 100 kHz.

16. The system according to claim 12 where the FAF light source is a superluminescent diode.

17. The system according to claim 12 where the FAF light source is a broadband LED.

18. The system according to claim 12 where the FAF light source operates between 535-585 nm.

* * * * *